(12) United States Patent
Hua et al.

(10) Patent No.: US 10,990,808 B2
(45) Date of Patent: Apr. 27, 2021

(54) FACE LIVENESS DETECTION USING BACKGROUND/FOREGROUND MOTION ANALYSIS

(71) Applicant: AWARE, INC., Bedford, MA (US)

(72) Inventors: Fang Hua, Bedford, MA (US); Taras Riopka, Concord, MA (US)

(73) Assignee: AWARE, INC., Bedford, MA (US)

( * ) Notice: Subject to any disclaimer, the term of this patent is extended or adjusted under 35 U.S.C. 154(b) by 120 days.

(21) Appl. No.: 16/071,026

(22) PCT Filed: Feb. 8, 2017

(86) PCT No.: PCT/US2017/016927
§ 371 (c)(1),
(2) Date: Jul. 18, 2018

(87) PCT Pub. No.: WO2017/139325
PCT Pub. Date: Aug. 17, 2017

(65) Prior Publication Data
US 2019/0026544 A1    Jan. 24, 2019

Related U.S. Application Data

(60) Provisional application No. 62/292,930, filed on Feb. 9, 2016.

(51) Int. Cl.
*G06K 9/00* (2006.01)
*A61B 5/11* (2006.01)
(Continued)

(52) U.S. Cl.
CPC ........ *G06K 9/00288* (2013.01); *A61B 5/0077* (2013.01); *A61B 5/1128* (2013.01);
(Continued)

(58) Field of Classification Search
CPC .......... G06K 9/00288; G06K 9/00906; G06K 9/6202; G06K 9/34; G06T 7/194;
(Continued)

(56) References Cited

U.S. PATENT DOCUMENTS

| 2009/0060277 A1* | 3/2009 | Zhang | G08B 13/19606 382/103 |
| 2013/0188840 A1* | 7/2013 | Ma | G06K 9/00261 382/107 |
| 2018/0349682 A1 | 12/2018 | Wong et al. | |

FOREIGN PATENT DOCUMENTS

| CN | 107317952 A | 11/2017 |
| WO | WO 2017/139325 | 8/2017 |

OTHER PUBLICATIONS

Anjos, André, and Sebastien Marcel. "Counter-measures to photo attacks in face recognition: a public database and a baseline." In 2011 international joint conference on Biometrics (IJCB), pp. 1-7. IEEE, 2011.*

(Continued)

*Primary Examiner* — Zhitong Chen
(74) *Attorney, Agent, or Firm* — Jason H. Vick; Sheridan Ross, PC

(57) ABSTRACT

Face recognition systems are vulnerable to the presentation and spoofed faces, which may be presented to face recognition systems, for example, by an unauthorized user seeking to gain access to a protected resource. A face liveness detection method that addresses this vulnerability utilizes motion analysis to compare the relative movement among three regions of interest in a facial image, and based upon that comparison to make a face liveness determination.

20 Claims, 15 Drawing Sheets

(51) Int. Cl.
| | |
|---|---|
| A61B 5/1171 | (2016.01) |
| A61B 5/00 | (2006.01) |
| G06T 7/194 | (2017.01) |
| G06T 7/11 | (2017.01) |
| G06T 7/246 | (2017.01) |
| G06N 20/00 | (2019.01) |
| G06K 9/62 | (2006.01) |
| G06K 9/34 | (2006.01) |

(52) U.S. Cl.
CPC ........ *A61B 5/1176* (2013.01); *G06K 9/00906* (2013.01); *G06K 9/6202* (2013.01); *G06N 20/00* (2019.01); *G06T 7/11* (2017.01); *G06T 7/194* (2017.01); *G06T 7/246* (2017.01); *G06K 9/34* (2013.01); *G06T 2207/30201* (2013.01)

(58) Field of Classification Search
CPC . G06T 7/11; G06T 7/246; G06T 2207/30201; G06N 20/00; A61B 5/0077; A61B 5/1128; A61B 5/1176
See application file for complete search history.

(56) References Cited

OTHER PUBLICATIONS

Anjos, André, Murali Mohan Chakka, and Sébastien Marcel. "Motion-based counter-measures to photo attacks in face recognition." IET biometrics 3, No. 3 (2013): 147-158.*

Bao, Wei, Hong Li, Nan Li, and Wei Jiang. "A liveness detection method for face recognition based on optical flow field." In 2009 International Conference on Image Analysis and Signal Processing, pp. 233-236. IEEE, 2009.*

Anjos, André, and Sebastien Marcel. "Counter-measures to photo attacks in face recognition: a public database and a baseline." In 2011 international joint conference on Biometrics (IJCB), pp. 1-7. IEEE, 2011 (Anjos2).*

International Preliminary Report on Patentability for International Application No. PCT/US2017/016927, dated Aug. 23, 2018.

Anjos, André et al "Motion-Based Counter-Measures to Photo Attaches in Face Recognition" IET Biometrics, vol. 3, Issue 3, Sep. 2014; pp. 147-158.

Bharadwaj, Samarth et al "Computationally Efficient Face Spooling Detection with Motion Magnification" 2013 IEEE Conference on Computer Vision and Pattern Recognition Workshops; Jun. 23, 2013; pp. 105-110.

Kim, Younghwan, et al. "A Motion and Similarity-Based Fake Detection Method for Biometric Face Recognition Systems" IEEE Transactions on Consumer Electronics, vol. 57, Nov. 2, May 2011.

Yan, Junjie et al. "Face Liveness Detection by Exploring Multiple Scenic Clues" 2012 12th International Conference on Control, Automation, Robotics, & Vision; Guangzhou, China; Dec. 5-7, 2012.

International Search Report for International Application No. PCT/US2017/016927, dated May 17, 2017.

Written Opinion for International Application No. PCT/US2017/016927, dated May 17, 2017.

International Application No. PCT/US2019/064635, filed Dec. 5, 2019.

Bales, M. Ryan et al. "BigBackground-Based Illumination Compensation for Surveillance Video" Eurasip Journal on Image and Video Processing; vol. 2011; Dec. 21, 2010.

Li, Xiaobai et al. "Remote Heart Rate Measurement from Face Videos Under Realistic Situations" IEEE Conference on Computer Vision and Pattern Recognition; Jun. 23, 2014.

Torres, Juan et al,."Linear Colour Correction for Multiple Illumination Changes and Non-Overlapping Cameras" IET Image Processing, IET, vol. 9. No. 4, Apr. 1, 2015.

Office Action for European Application No. 17705764.3, dated Apr. 8, 2020.

International Search Report for International Application No. PCT/US2019/064635, dated Feb. 20, 2020.

Written Opinion for International Application No. PCT/US2019/064635, dated Feb. 20, 2020.

\* cited by examiner

FACE LIVENESS DETECTION USING BACKGROUND/FOREGROUND MOTION ANALYSIS

RELATED APPLICATION DATA

This application is a national stage application under 35 U.S.C. 371 of PCT Application No. PCT/US2017/016927, filed Feb. 8, 2017, which designated the United States, which PCT application claims the benefit of and priority under 35 U.S.C. § 119(e) to U.S. Patent Application No. 62/292,930, filed Feb. 9, 2016, entitled "FACE LIVENESS DETECTION USING BACKGROUND/FOREGROUND MOTION ANALYSIS," each of which are incorporated herein by reference in their entirety.

BACKGROUND

Biometrics refers to the process of verifying or identifying individuals' identity based upon one or more intrinsic physical characteristics such as faces, fingerprints, irises, voices, etc. Face recognition is a process for verifying or identifying a person from provided images. It has gained great attention due to its wide variety of applications in security, law enforcement, and entertainment. Compared to other biometric matchers, e.g. iris and fingerprint, face recognition has distinct advantages because of its non-invasive and user friendly nature. Face images acquired from a distance can be used for face recognition. The process of verification and identification for face recognition also requires little or no cooperation from the user. As technology continues to develop, devices for acquiring high quality face images are becoming less expensive and smaller in size, expanding their use in various applications, e.g. smart phone, sports accessories, etc. However, face images and face videos are also becoming widely available throughout the Internet due to the popularity of social networks. This simplifies and expands access to face images that can potentially be used to spoof face recognition systems. Since face recognition systems are vulnerable to spoof attacks made by recorded static facial images and/or videos, it is important to have secure methods to protect biometric authentication systems against such spoofs.

Current face recognition biometric systems allow a face enrollment step in which a face image is captured and stored. Face detection is used to detect the face. Finally, face matching is performed to compare the detected face with other faces from a database to identify the identity. This type of face recognition system generally does not provide enough algorithm intelligence to differentiate a live face from a spoofed image for face matching. Identity fraud can occur when a spoofed face matches an identity in the database successfully.

To prevent spoof attacks using facial images, as well as to enhance the reliability of face recognition systems, face liveness detection is of great importance. Face liveness detection is designed to detect live signs (e.g., signs that a facial image is an image of a living person's actual face, rather than an image of an image of a face) to guard against attempted misrepresentation of identity using spoofed facial images. Spoof attacks using cosmetic masks are not considered for the discussion here.

Although many types of spoofs exist, face liveness detection methods are primarily divided into two groups: active methods and passive methods.

Active methods for face liveness detection require cooperative interaction between the target subject and the liveness detection system. The face liveness detection system provides one or multiple instructions requesting some type of cooperative behavior, such as blinking of the eyes, mouth/lip movement, and turning of the head. Successful responses exhibiting this behavior are considered to be a sign of life. A failure to respond, or an incorrect response to a system's instruction, may indicate an inability to perform the desired behavior, which may in turn be evidence of spoofing. There are two disadvantages to active methods. First, active methods diminish the benefit of the non-intrusive nature of face recognition systems by requiring more subject cooperation. Second, active face liveness detection methods that require a response to instructions may be easily spoofed by replaying a video of a person complying with the instructions if instructions are known.

In contrast to interactive methods for face liveness detection, passive face liveness detection methods do not require subject cooperation or interruption during the analysis process. Passive face liveness detection methods base their spoof/liveness decision on image analysis data obtained unobtrusively from image data of the subject. Various methods have been discussed in the literature. Some passive methods look for boundaries of cell phones, displays or other potential features of spoofs. Still others analyze the affine transform of facial feature locations to look for evidence of non-planar surfaces. However, most of the passive face liveness detection methods only detect one or very few specific spoofing types, such as a printed photo or a smart phone static image or replay video, by detecting a boundary (e.g. a boundary of the printed photo or of the smart phone screen). If new spoofing media are presented to the system, false detection may occur due to lack of knowledge of this new spoofing media.

In general, both active and passive face liveness detections in use today suffer from limited usage and lack of efficiency due to various problems. Hence, a more general and efficient face liveness detection method is needed to provide more security to the face recognition system.

BRIEF DESCRIPTION OF THE DRAWINGS

The exemplary embodiments of the technology will be described in detail, with reference to the following figures wherein.

DETAILED DESCRIPTION

Figure 1A:
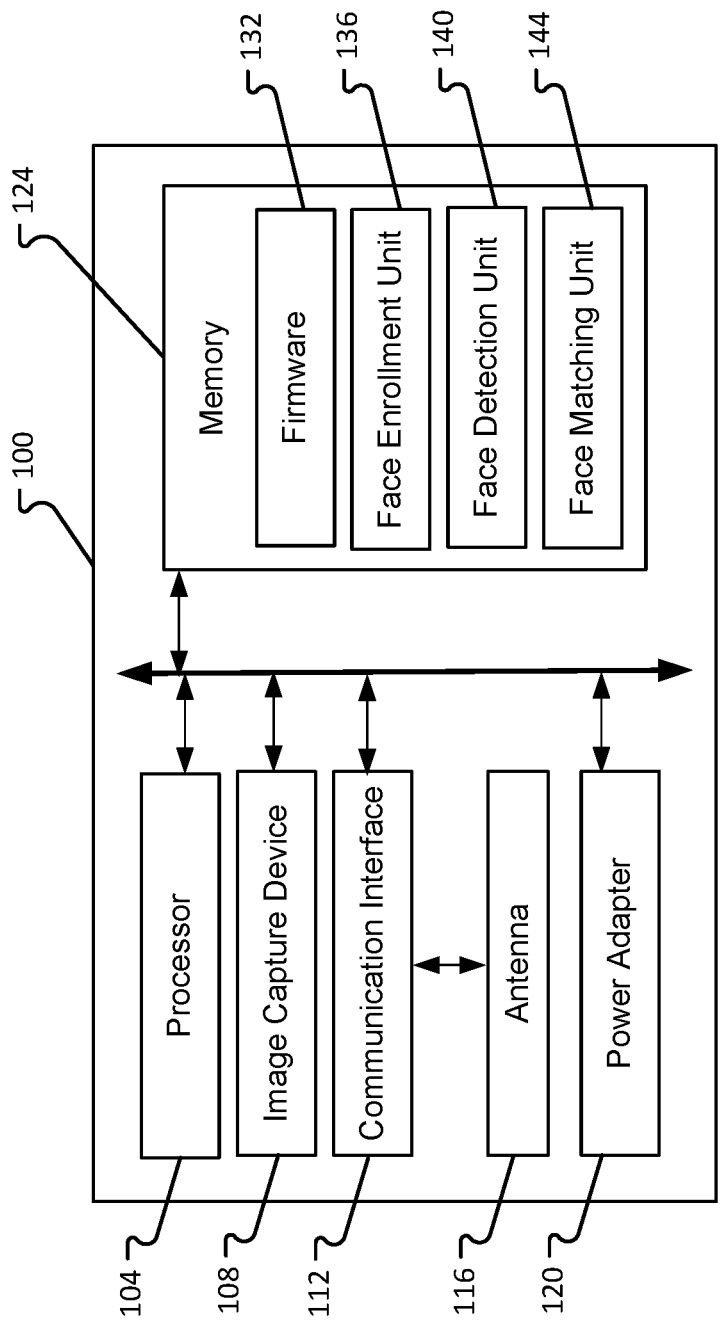
FIG. 1A shows a block diagram of a system according to one embodiment of the present disclosure.

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Terminology

Biometrics: the process of verifying or identifying individuals' identity based upon one or more intrinsic physical characteristics such as faces, fingerprints, irises, voices, etc.
Face Recognition: a process of identifying a person, or verifying a person's identity, from provided images of the person's face.
Face Recognition System: A biometric system based on face recognition. In some embodiments, a face recognition system may be integrated or otherwise interconnected with an access control system, and used to distinguish authorized users from unauthorized users by facial analysis.
Live Face: A face of a living being that may be or is presented directly to a face recognition system (as opposed to a spoofed face).
Spoof/Spoofed Face: An image of a face that may be or is presented to a face recognition system. For example, an unauthorized user may present a picture of an authorized user (a spoof) to a face recognition system in an attempt to gain illicit access to a resource protected by the system.
Spoofing Medium/Media: Any medium or media upon which a spoof is provided, including but not limited to a paper, a photo paper, a shaped board, a display monitor (e.g. a computer monitor, television, or display screen), and smart phone.

A significant drawback of current face recognition systems is that if a spoofed face can pass through the face detection unit, it may be treated no differently from a live face. Once a face is detected, various image transformation methods may be applied, e.g. image rotation, resizing, grayscale conversion, noise filtering or pose correction, etc. These image processing steps may reduce or filter out possible spoofing features or patterns needed to differentiate live faces from spoofed faces. The challenge is, therefore, to analyze the input image and obtain useful spoofing knowledge to differentiate live face and spoof face in earlier stages of the face recognition system.

As discussed in more detail below, the present disclosure describes methods that include searching for regions of interest based on the location of the face to obtain three related but disjoint segmented regions; utilizing Optical Flow (or similar motion estimation features) to do motion analysis and extract motion features in the three segmented regions; and measuring and characterizing motion interactions between regions taking into account the background as the reference to discriminate between live and spoofed faces.

Referring first to FIG. 1A, a face recognition device 100 according to one embodiment of the present disclosure may comprise a processor 104, an image capture device 108, a communication interface 112 (which may or may not comprise an antenna 116), a power adapter 120, and a memory 124.

The processor 104 may correspond to one or multiple microprocessors that are contained within a housing of the device 100. The processor 104 may comprise a Central Processing Unit (CPU) on a single Integrated Circuit (IC) or a few IC chips. The processor 104 may be a multipurpose, programmable device that accepts digital data as input, processes the digital data according to instructions stored in its internal memory, and provides results as output. The processor 104 may implement sequential digital logic as it has internal memory. As with most known microprocessors, the processor 104 may operate on numbers and symbols represented in the binary numeral system. The processor 104 may be configured to execute instructions stored in the memory 124.

The image capture device 108 captures images of faces that are subsequently provided as inputs to one or more of the face enrollment unit 136, face detection unit 140, and face matching unit 144. The image capture device 108 may comprise a camera, a videocamera, and/or one or more other optical sensors, and may use, for example, charge-coupled device (CCD) or complementary metal-oxide semiconductor (CMOS) image sensors. Images captured by the image capture device 108—which images may be still images or videos—may be stored in the memory 124. In addition to image sensors, the image capture device 108 may comprise one or more sensors configured to enhance the quality of images captured by the image capture device 108, such as light meters (e.g., for adjusting exposure), distance meters (e.g., for detecting distance to subject), contrast sensors (e.g., for autofocus), lighting device (e.g., for illuminating the subject in different spectrums), and motion detectors (e.g., for triggering image capture). The image capture device 108 may be configured for continuous operation, or for periodic operation, or for on-command operation. In some embodiments, for example, the image capture device 108 may capture images only when directed to do so by the processor 104 upon execution by the processor 104 of instructions from one or more of the face enrollment unit 136, the face detection unit 140, and the face matching unit 144. Also in some embodiments, the image capture device may provide, under the control of the processor 104, a continuous video feed that is continuously monitored by the processor 104 (according to instructions executed by the processor 104 from one or more of the face enrollment unit 136, the face detection unit 140, and the face matching unit 144), and may capture and store images only at the command of the processor 104.

The face recognition device 100 may comprise a communication interface 112, which may be used, for example, to communicate with a central server and/or with the cloud. The communication interface 112 may beneficially enable the face recognition device 100 to access remote storage (e.g. for storing and/or archiving captured image information, face enrollment information, face detection information, and/or face matching information), to receive commands from a central control system (e.g. an offsite server or administrator), to access databases or other repositories of facial images for matching/recognition purposes, and/or to transmit face recognition determinations or related information (e.g. authorization/no authorization decisions) to a central database for storage and/or analysis, to an administrator, operator, or other user, and/or to an access control system or access control system component (e.g. an electrically actuated door lock).

The communication interface 112 may utilize any known wired or wireless communication protocol. Examples of wired protocols that may be utilized by the communication interface 112 include RS-232, RS-422, RS-485, I2C, SPI, IEEE 802.3, and TCP/IP. Examples of wireless protocols that may be utilized by the communication interface 112 include IEEE 802.11a/b/g/n, Bluetooth, Bluetooth Low Energy (BLE), FeliCa, Zigbee, GSM, LTE, 3G, 4G, 5G, RFID, and NFC. The communication interface 112 may comprise hardware (e.g. an Ethernet port, a wireless radio), software (e.g. drivers, firmware, applications), or a combination thereof to enable communications to and from the face recognition device 100. Where the communication interface 112 uses a wireless communication protocol, the communication interface 112 may also comprise an antenna 116 for sending and receiving signals wirelessly.

The power adapter 120 receives power (e.g., electricity) from an external source and routes the power to the various components of the face recognition device 100 as needed, while also performing power transformation and signal conditioning functions as necessary to ensure that power is provided to each component of the face recognition device 100 according to the specifications of the component in question. In some embodiments, the power adapter 120 may comprise a backup power source (e.g., one or more batteries, a generator, a solar cell) for ensuring the continuous provision of power to the face recognition device 100, even if the primary power source (which may be, for example, a public electricity grid) is interrupted.

The memory 124 may correspond to any type of non-transitory computer-readable medium. In some embodiments, the memory 124 may comprise volatile or non-volatile memory and a controller for the same. Non-limiting examples of memory 124 that may be utilized in the device 100 include RAM, ROM, buffer memory, flash memory, solid-state memory, or variants thereof.

The memory 124 stores any firmware 132 needed for allowing the processor 104 to operate and/or communicate with the various components of the face recognition device 100, as needed. The firmware 132 may also comprise drivers for one or more of the components of the device 100.

In addition, the memory 124 may store one or more modules for carrying out the various steps described herein. For example, the memory 124 may store a face enrollment unit or module 136 that contains instructions for causing the processor 104 to command the image capture device 108 to capture an image. The face enrollment unit 136 may further cause the processor 104 to analyze the image, detect a face within the image, generate a normalized face image, associate identification information (e.g. name, birthday, identification number, access privileges) with the normalized face image, and store the normalized face image and associated identification information for future reference.

As another example, the memory 124 may store a face detection unit or module 140 containing instructions that, when executed by the processor, allow the processor to identify one or more faces within an image captured by the image capture device 108, and to generate a normalized face image of such faces. The face detection unit 140 may, for example, be accessed by one or both of the face enrollment unit 136 and the face matching unit 144 whenever the functions of the face detection unit 140 are necessary. In some embodiments, the face detection unit 140 may cause the processor 104 to continuously monitor a continuous video feed from the image capture device 108, and may cause the processor 104 to instruct the image capture device 108 to obtain still images whenever one or more faces are detected in the continuous video feed. The face detection unit 140 may further cause the processor to generate a normalized face image of faces detected in such images, and may cause the processor 104 to activate the face matching unit 144 for analysis of such normalized face images.

The memory 124 may further store a face matching unit or module 144. The face matching unit or module 144 may be configured to analyze a normalized face image (or, in some embodiments, to first generate a normalized face image using an image obtained via the image capture device 108), including by comparing the normalized face image to known faces (e.g. faces that have been enrolled via the face enrollment unit 136, and/or faces obtained from an external database or repository via the communication interface 112). When a normalized face matches a known face, the face matching unit 144 may further be configured to transmit information about the match to an administrator, operator, or other user of the face recognition device 100 via the communication interface 112, and/or may further be configured to selectively transmit a control signal to an access control system or access control system component. For example, if a match is identified, the face matching unit 144 may check the identification information associated with the enrolled facial image that matches the identified facial image, determine whether the identification information indicates that the person associated with the enrolled facial image has access privileges, and grant or deny access (e.g. by controlling an electrically actuated door lock) based on the determination.

In embodiments of the present disclosure, one or more of the face enrollment unit 136, the face detection unit 140, and the face matching unit 144 may be configured to conduct face liveness detection as described herein. Where each unit 136, 140, and 144 operates a stand-alone unit (e.g. without utilizing the other units to complete the face enrollment, face detection, and face matching functions), each unit 136, 140, and 144 may be configured to conduct face liveness detection. Where each unit 136, 140, and 144 has unique functions, and the three units 136, 140, and 144 operate together to provide the face enrollment, face detection, and face matching functions, only one unit 136, 140, or 144 may be configured to conduct face liveness detection. For example, the face detection unit 140 may be configured to conduct face liveness detection for each face detected in an image, prior to that face (or data corresponding thereto) being provided to the face enrollment unit and/or the face matching unit 144 for further analysis.

Figure 1B:
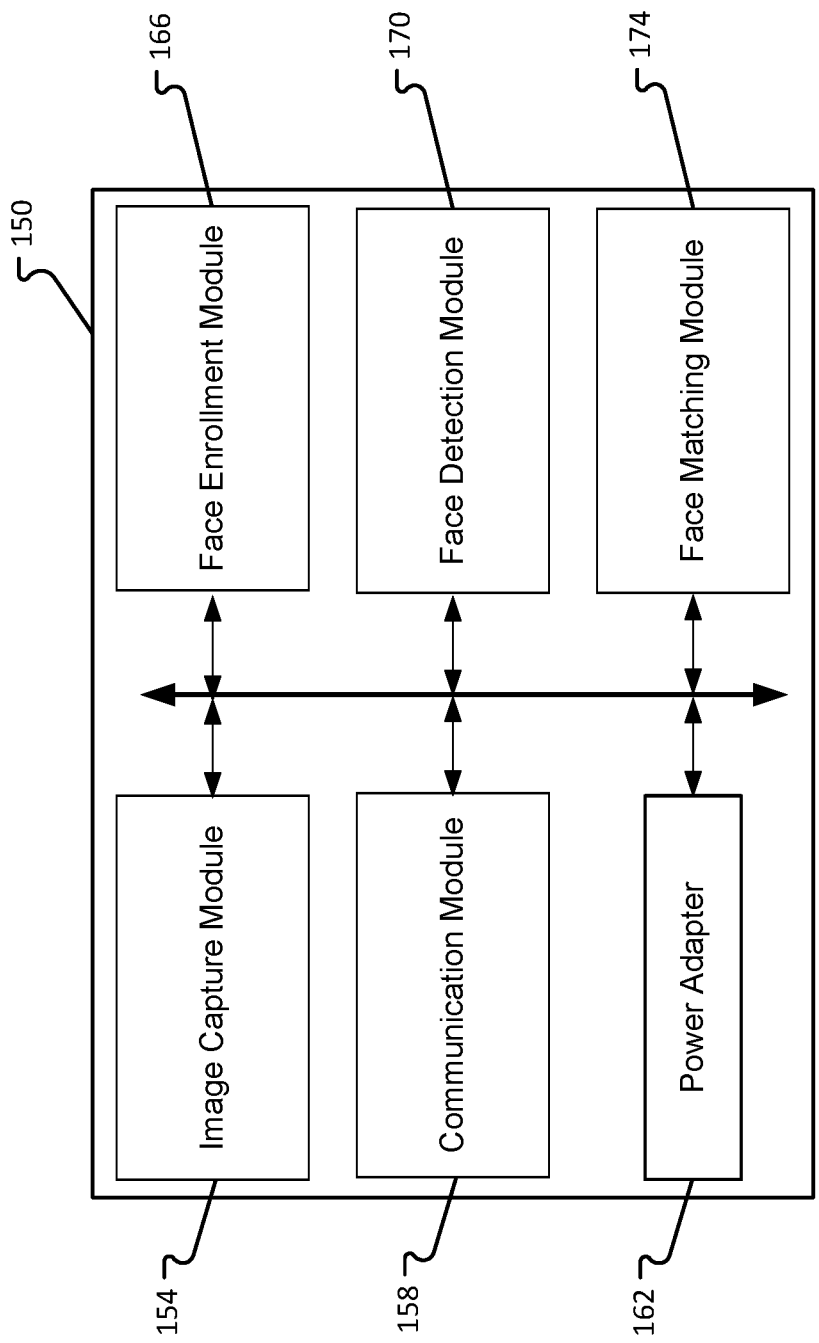
FIG. 1B shows a block diagram of a system according to another embodiment of the present disclosure.

Turning to FIG. 1B, a face recognition device 150 according to another embodiment of the present disclosure may utilize one or more application-specific integrated circuits, rather than a processor that executes instructions from multiple units. Such application-specific integrated circuits may be combined with appropriate hardware to form one or more modules for carrying out specific tasks. For example, the face recognition device 150 comprises an image capture module 154, a communication module 158, a power adapter 162, a face enrollment module 166, a face detection module 170, and a face matching module 174.

The image capture module 154 may comprise an image capture device (e.g. a camera or video camera or other image capture device), which may use any known or available image capture technology (including CMOS and/or CCD sensors). Other sensors, such as those described in connection with the image capture device 108 described above, may also be included in the image capture module 154.

The image capture module 154 may further comprise a processor controlling operation of the image capture module and one or more memory blocks for storing information, such as instructions for execution by the processor, firmware for operating the image capture device, and images captured by the image capture device. The image capture device may be large or small in size. For example, in some embodiments, the image capture module may be sufficiently small to be placed in a normally-sized writing utensil, or otherwise placed to avoid ready detection. In other embodiments, the image capture module may be mounted on a wall or ceiling and readily visible. Also in some embodiments, the image capture module 154 may be utilized for purposes other than those of the face recognition device 150. For example, a smartphone may comprise an image capture module 154 that may be used to take and store photos and/or videos as well as for face recognition purposes as described herein.

The image capture module 154 may be configured to continuously provide time-stamped image frame sequences to one or more of the face enrollment module 166, face detection module 170, and/or face matching module 174. Alternatively, the image capture module 154 may be configured to provide a time-stamped image frame sequence to one or more of the face enrollment module 166, the face detection module 170, and/or the face matching module 174 upon receipt of a command from a central administrator (e.g. via the communication module 158) or from one or more of the modules 166, 170, and 174. In some embodiments, the image capture module 154 may periodically send an image to one or more of the modules 166, 170, and 174, and may receive in response a command to obtain and provide a time-stamped image frame sequence to one or more of the modules 166, 170, 174.

The communication module 158 may comprise one or more wired communication ports and/or a wireless communication radio and associated antenna. The communication module 158 may be configured to communicate over a wired communication port using, for example, a protocol such as RS-232, RS-422, RS-485, I2C, SPI, IEEE 802.3, or TCP/IP. In embodiments having a wireless communication radio, the wireless communication radio may be configured to communicate using any known wireless communication standard, including, for example, IEEE 802.11a/b/g/n, Bluetooth, Bluetooth Low Energy (BLE), FeliCa, Zigbee, GSM, LTE, 3G, 4G, 5G, RFID, and NFC. The communication module 158 may be used to send or receive information. For example, the communication module 158 may be used to receive information from remote databases containing known face images, and/or to receive firmware or software updates for any of the modules of the face recognition device 150, and/or to receive new or updated face classification rules, and/or to receive new or updated access control rules (for embodiments of the face recognition device 150 that control access to a protected resource, e.g. by selectively unlocking a door based on the results of a face recognition determination), and/or to transmit a face recognition determination to a central server or administrator, and/or to transmit stored images captured by the image capture module 154 for offline storage or remote review.

The power adapter 162 may be the same as or similar to the power adapter 120. The power adapter 162 provides power (e.g. electricity) to the various modules of the face recognition device 150. In some embodiments, the power adapter 162 receives a first power signal from an outside source and sends one or more second, distinct power signals (e.g. power signals obtained by transforming, conditioning, or otherwise modifying the incoming first power signal) to one or more modules of the face recognition device 150. The power adapter may comprise a backup power source, such as a battery, and may also comprise one or more power generation units (e.g. a solar panel).

The face enrollment module 166 may comprise a processor and one or more memory blocks containing, for example, instructions for execution by the processor as well as data received from another module or from a remote database (e.g. via the communication module 158), or for transmission to another module or to a remote database (e.g. via the communication module 158). The instructions may be configured to cause the processor to receive an image captured by the image capture module 154, analyze the captured image to identify relevant features thereof (e.g. features that may be useful or necessary for face recognition purposes), and store (or cause to be stored) information about the identified features for future use or reference. The face enrollment module may comprise a user interface for allowing a user to indicate when a new face is to be enrolled. The face enrollment module may also comprise one or more security features (e.g. password protection, biometric protection, time-based access control, authentication requirements) to prevent unauthorized enrollment of a new face. The user interface may be physical (e.g. a button or a keypad) or electronic (e.g. for receiving commands via the wireless communication module 158 from an external computer or terminal).

In some embodiments, the face enrollment module 166 may communicate or otherwise operate in conjunction with the face detection module 170 when enrolling a new face to ensure that the face presented for enrollment is a live face, using the methods described in greater detail herein.

The face detection module 170 may also comprise a processor and one or more memory blocks containing, for example, instructions for execution by the processor as well as data received from another module or from a remote database (e.g. via the communication module 158), or data for transmission to another module or a remote database (e.g. via the communication module 158). The instructions may cause the processor to detect one or more faces in an image or image sequence received from the image capture module 154. The instructions may also cause the processor to make a face liveness determination for one or more faces detected in an image or image sequence received from the image capture module 154, using, for example, the methods described herein. The instructions may also cause the processor to transmit the results of a face detection and/or of a face liveness determination to the face recognition module 174, the face enrollment module 166, and/or to a remote recipient (e.g. a central administrator or database) via the communication module 158.

The face matching module 174, like the modules 166 and 170, may comprise a processor and one or more memory blocks containing, for example, instructions for execution by the processor as well as data received from another module or from a remote database (e.g. via the communication module 158), or data for transmission to another module or a remote database (e.g. via the communication module 158). The instructions may cause the processor to compare information from or about a detected or new face image with information from or about face images corresponding to known faces, for the purpose of determining whether the detected or new face image is an image of a known face. The instructions may also cause the processor to communicate with a remote database of known faces, and/or to communicate a face recognition determination to an access control system, and/or to a central database or repository.

Memory blocks included in the various modules of the face recognition device 150 may be any non-transient, tangible form or type of memory. For example, the memory blocks may be or comprise ROM, RAM, EEPROM, and/or flash memory.

The face recognition devices 100 and 150 are not intended to be mutually exclusive embodiments of the present disclosure. Aspects of the face recognition device 100, as described above, may be incorporated into the face recognition device 150. Similarly, aspects of the face recognition device 150, as described above, may be incorporated into the face recognition device 100.

Figure 2:
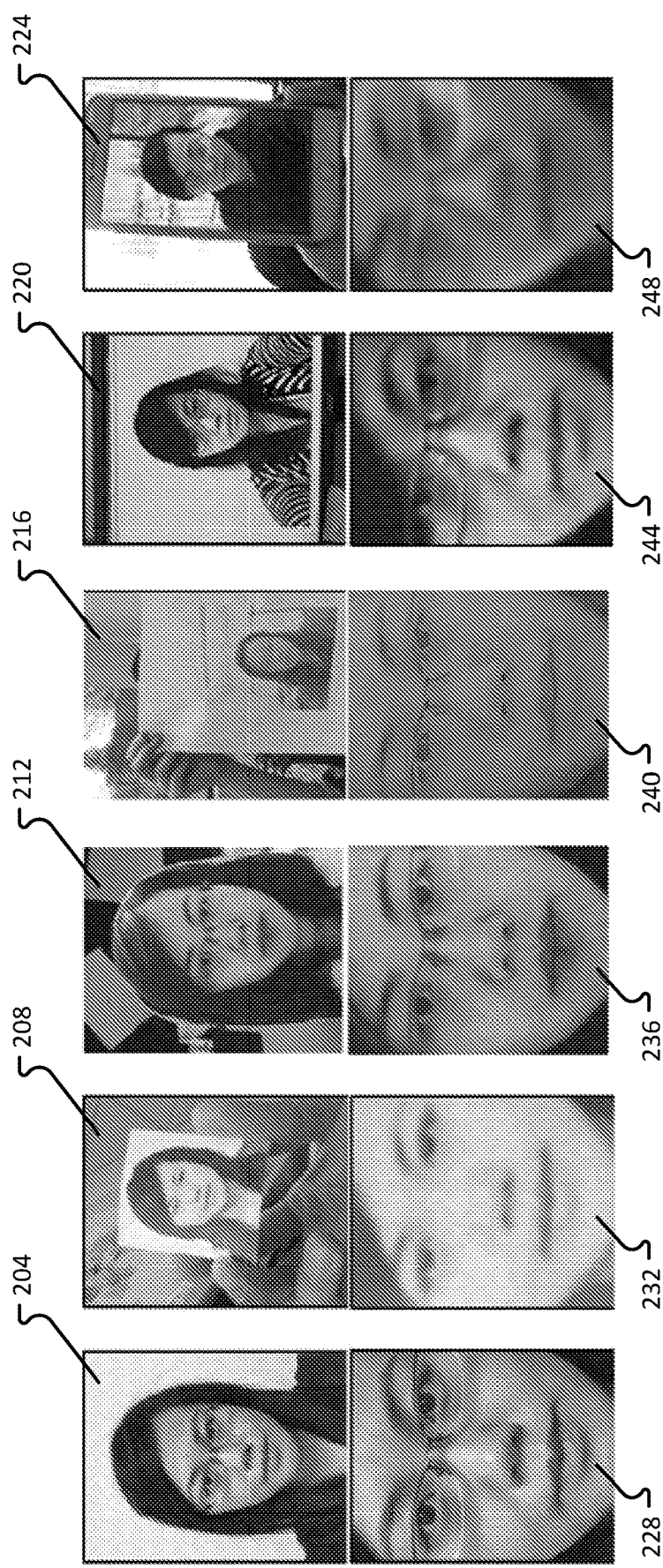
FIG. 2 shows images of a live face and a plurality of spoofing images, together with a corresponding normalized face region for each.

With reference now to FIG. 2, two rows of images are depicted. The top row, comprising images 204 through 224, contains images such as those that might be captured by a face detection unit 140 using an image capture device 108 of a face recognition device 100, or by an image capture module 154 of a face recognition device 150. Image 204 is a live face. Image 208 is a printed photo spoof; image 212 is a printed shape board spoof; image 216 is a printed paper spoof; image 220 is a static digital image spoof; and image 224 is a smart phone replay video spoof. The bottom row, comprising images 228-248, shows normalized face images processed by a face recognition unit 132 after capture of the images 204 through 224 by the face detection unit 128. Each column of FIG. 2 contains a captured face image (e.g. image 204) and the corresponding normalized face image (e.g. image 228). Except for some quality issues apparent in the normalized face images, e.g. blur (images 232, 244, and 248), washed out (image 232), etc., it is almost impossible to determine whether the face region shown in the normalized face images 228 through 248 is from a live face or a spoofed face.

Given the limitations of existing active and passive face liveness detection methods, an efficient method is needed that utilizes more general information across different spoofing media and can differentiate various types of spoofs from live images.

To solve the problems discussed above and herein, the present disclosure provides a new passive face liveness detection method that utilizes more general knowledge from a captured face image to detect spoofing. The proposed method neither depends on the detection of specific spoofing features, e.g. a smartphone boundary or a photo boundary, nor relies on a single facial feature movement, e.g. blink, mouth movement, head turning around, etc. Instead, the present disclosure is based on the knowledge that the motion of the face region and the background are highly correlated for spoofed images, and uncorrelated for live faces. By analyzing the motion characteristics of the face region and of the background, the present disclosure utilizes the global knowledge from the image, taking the background as the reference, to detect spoofing. The present disclosure can be generalized and made robust across different spoofing types.

The background reference method for face liveness detection disclosed herein focuses on the interaction of motions between the face, any non-background media (e.g. spoofing media), and the background. Motion analysis information with respect to the face region and other regions of interest associated with the non-background media and the true background is measured, characterized and used to differentiate between spoofed and live facial data.

When an acquisition camera or other image capture device 108 is fixed to capture facial images (such that the background is not moving), the face region of a spoof moves with the region close to the head which usually contains spoofing media (e.g., because the face is printed on the spoofing media, as with a handheld printed photo or paper or a handheld smart phone video replay) Meanwhile, the region close to the head in a spoof also moves with the background, while the background has significantly more movement than does a true background (e.g. because the face is presented via, for example, a static screen display).

Figure 3:
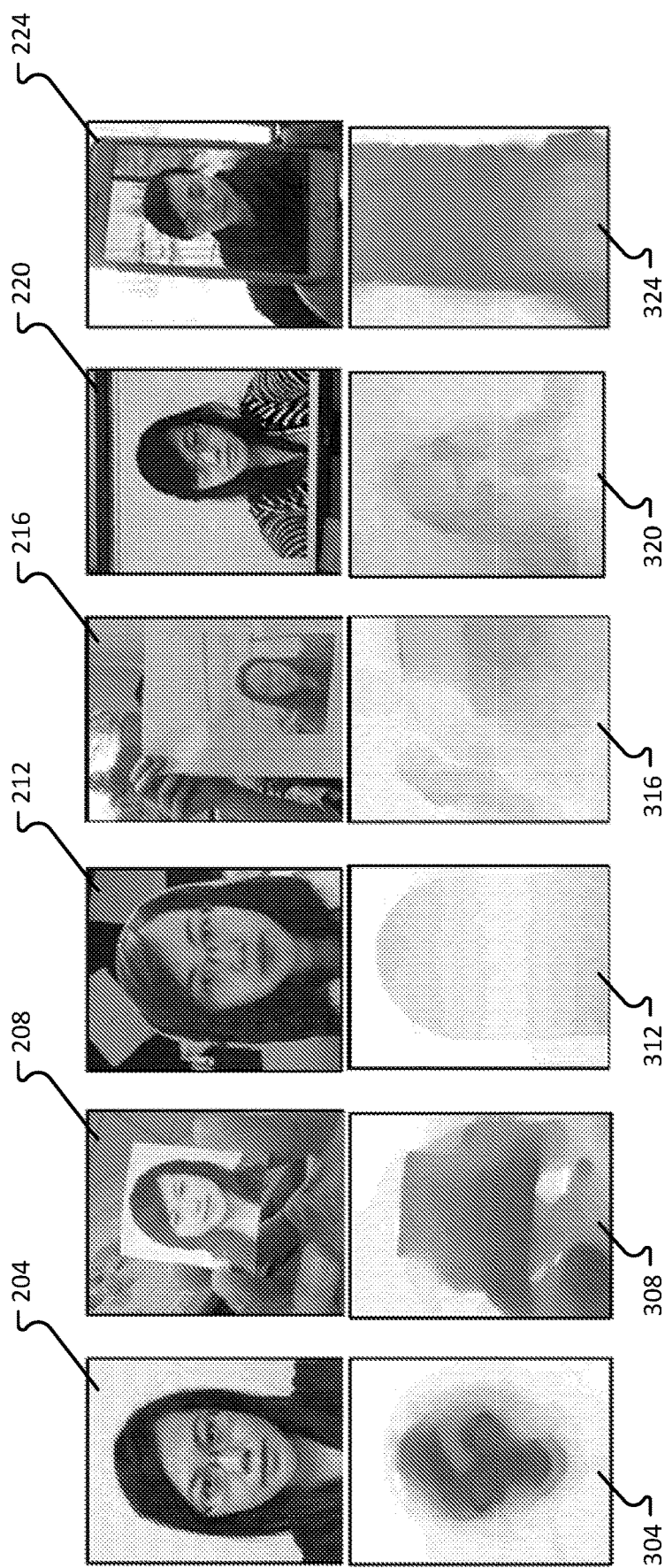
FIG. 3 shows images of a live face and a plurality of spoofing images, together with a corresponding visualized motion image for each.

This principle can be observed in FIG. 3, where the captured images 204 through 224 are displayed above visualized motion images 304 through 324 from video streams of the corresponding captured image. Thus, for example, visualized motion image 304 corresponds to captured live face image 204; visualized motion image 308 corresponds to captured printed photo image 208; and so forth. Colorful regions represent areas of movement, while white regions represent areas of no movement. As depicted in image 304, a live face shows movement in the camera foreground, whereas the background (located behind the subject) shows no movement. The subject and background are therefore said to have uncorrelated motion (because the movement of the face has no correlation to any movement of the background).

The same is not true with respect to several of the spoof attempts. For example, the print photo, print paper spoof attempts, and cell phone spoofing, depicted in images 208 and 308, in images 216 and 316, and in images 224 and 324, respectively, show highly correlated, if not identical, movement of the face region and regions close to the head (including the background of print photo, the edges of the spoofing media, and the hands that are holding the spoofing media). Even the shape board spoof attempt, depicted in images 212 and 312, shows highly correlated, if not identical, movement of the face region and nearby regions (including the neck and shoulder areas of the shape board). When a display screen is used as the spoofing medium (as depicted in image 220) with a static image displayed thereon, there is correlated movement of the face region, regions close to the head and the background (as depicted in image 320).

Difficulties arise in large screen spoofs where the boundary of the device is not visible to the analyzing algorithm. In such a case, there is no background separate from the spoof medium there to be analyzed. However, these types of spoofs (i.e. video replay on a large screen or high resolution screen) can show very similar correlations between the face region and the background for live data, but contain artificial patterns, e.g. Moiré patterns or other frequency related features, etc., that can have different image motion characteristics than live data. These scenarios are not as readily detectable as the other spoofs discussed herein but may nevertheless be detected with the proposed method.

Figure 4:
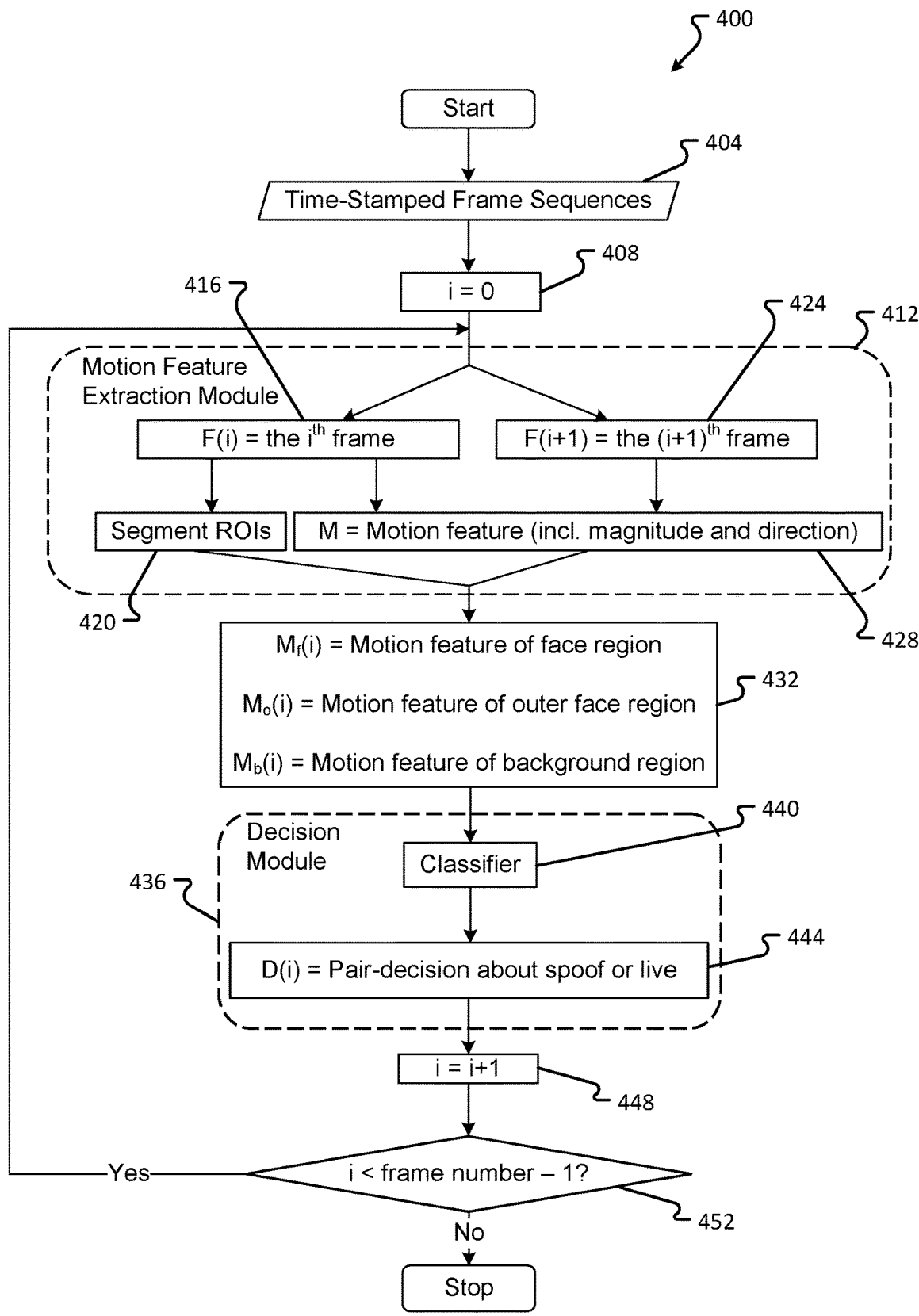
FIG. 4 shows a flowchart of a face liveness detection method according to one embodiment of the present disclosure.

FIG. 4 shows the work flow of a passive face liveness detection method 400 which relies upon motion analysis, according to embodiments of the present disclosure. The purpose of motion analysis is to extract information from the movement within a video stream. It is a crucial step towards understanding spoofing media or subject behaviors within the image at the pixel level.

In the method 400, which may be carried out, for example, by a processor 104 executing instructions from a face detection unit 140, a time-stamped frame sequence is received (e.g. from the image capture device 108) at step 404. The time-stamped frame sequence must include at least two images, but may alternatively comprise any number of images greater than two. The images are time-stamped to ensure that they are analyzed in the proper order, as well as to allow the processor 104 to determine the frame rate at which the images were captured, and to make adjustments accordingly. In some embodiments, the images may be captured at high frame rates. For example, some time-stamped frame sequences may comprise images taken at intervals of 1/4000th of a second, or of 1/8000th of a second. In other embodiments, images may be captured with intervals of 1/100th of a second, or 1/10th of a second. The present disclosure encompasses the use of time-stamped frame sequences comprising images taken at any frame rate that allows for motion-based face liveness detection as described herein.

At step 408, a frame counter i is set to a value of zero, corresponding to the first-in-time frame in the time-stamped frame sequence. At step 416, the ith frame is received by the motion feature extraction module 412. The purpose of the motion feature extraction module 412 is to extract motion features for each pair of consecutive frames from the video stream, and then use them to help characterize and quantify the motion of objects. There are several different methods that can be applied to perform motion analysis. The Shearlet transform or other multidimensional wavelets, for example, can be used as motion feature descriptors to serve the same purpose. Optical Flow is also one of many methods that may be used to analyze motion behaviors. The key idea of optical flow is that each pixel in an image has a velocity, including speed and direction. Thus, the movement of the subject within a video stream can be analyzed.

The optical flow estimation method of the present disclosure determines the instantaneous velocity of image pixels between successive images. In the following equation, it is assumed that pixel intensities are translated from one frame to the next:

$$I(x,y,t) = I(x+\Delta x, y+\Delta y, t+\Delta t)$$

In the above equation, I(x, y, t) is the image intensity as a function of location (x, y) and time t. Δx and Δy are the location differences between two images frames; Δt is the time difference between two image frames. This yields an Optical Flow constraint:

$$\frac{\partial I}{\partial x}\Delta x + \frac{\partial I}{\partial y}\Delta y + \frac{\partial I}{\partial t}\Delta t = 0$$

which results in:

$$\frac{\partial I}{\partial x}V_x + \frac{\partial I}{\partial y}V_y + \frac{\partial I}{\partial t} = 0$$

Where $V_x$, $V_y$ are the velocity in x and y directions, and together comprise the variable V. Assuming the subject is moving, the change of locations will yield the change in intensities across pixels, and thus the optical flow can measure the speed and direction at each pixel.

By looking at the change of velocity between pixels in sequential frames, subject motion behaviors can be detected. If there is no subject motion, optical flow changes continuously across the region, which leads to no velocity changes. But, if a subject moves across frames in a video stream, a discontinuity in the motion field will be produced, resulting in a large velocity change. Estimation of velocities based on Optical Flow for pixels between sequential frames is referred to as the motion feature extraction step.

As will be understood in light of the present disclosure, a lower frame rate will result in a larger change for pixels in consecutive frames than for pixels in frames obtained using a higher frame rate. Clearly the lower frame rate results in more time between frames. This effectively results in a larger calculated velocity for lower frame rates. This has an effect on signal strength and thresholds for face liveness detection. As a result, the face recognition device 100 or 150 may adjust thresholds used for face liveness detection based on the frame rate at which a given time-stamped frame sequence is taken. Frame rates from 5 frames per second to 30 frames per second may be used, although other frame rates may also be used.

Additionally, quality issues can lead to complexities in brightness consistency estimation by optical flow. Varying lighting conditions and/or camera device noise can contribute significantly to image brightness variation and hence optical flow motion estimate error. In some embodiments, images from the time-stamped frame sequence may be normalized, including, for example, by adjusting the overall intensity of each successive image so that each image has the same overall intensity, thus allowing for the movement of individual pixels to be tracked more accurately. In other embodiments, changes in intensity of the image background may be identified and used to adjust overall image intensity and/or to better determine identify corresponding pixels between images. For example, if the background of a second image has a greater intensity than a background of a first image, then a face recognition device 100 or 150 may assume that all pixels in the second image will demonstrate a similar increase in intensity. That increase can then be discounted when comparing pixels from the second image and the first image for purposes of the optical flow analysis.

Another potentially complicating factor is face size. Since all regions of interest are determined based on the face and have a fixed size relative to the face size, the face size directly affects the size of all three regions of interest. The face region A has to include the actual face and should not exceed the size of the head. Therefore, the smaller the face size, the less motion information can be generated within a frame field of view for each region of interest, which increases the difficulty of motion analysis as a result of the diminished signal to noise ratio. In some embodiments, these three regions are normalized into fixed sizes to overcome this issue. However, down sampling or up sampling the image can introduce artifacts or noise which can affect the accuracy of motion analysis. In some embodiments, a face recognition system may be configured only to analyze faces that satisfy a minimum size threshold. In other embodiments, a face recognition system may be configured to change the threshold for face liveness detection for faces smaller than a predetermined size. The training process, described in greater detail below, may inform or determine how the face recognition system deals with faces smaller than a predetermined size.

Returning to the method 400, at step 416, $I_i(x, y, t)$ is determined for each pixel in the ith image. At step 420, the ith frame from a time-stamped frame sequence undergoes segmentation into regions of interest (ROIs). Careful segmentation into various regions of interest is an important step for measuring motion interactions between face and background in terms of optical flow. This relationship is important because it characterizes a diverse set of live and spoof scenarios.

Figure 6:
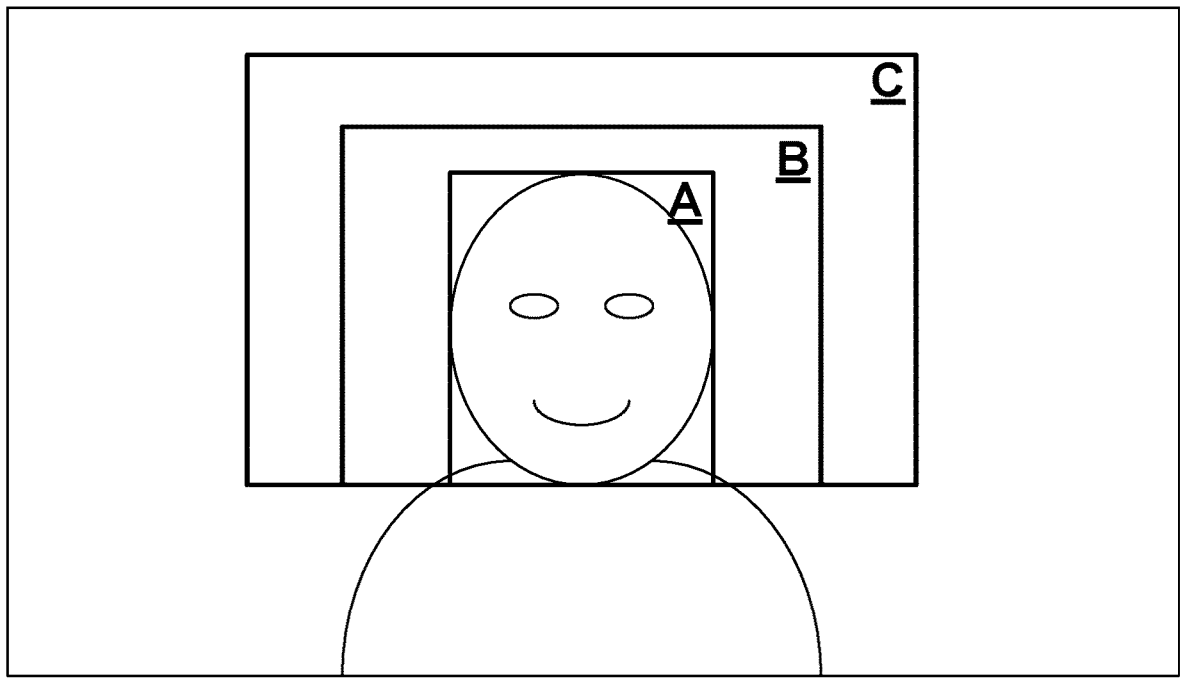
FIG. 6 is a diagram showing multiple regions of interest segmented from an image.

Referring briefly to FIG. 6, three primary regions of a given image are proposed for measurement and comparison: a face region A, a near-face region B, and a background region C. The face detection unit 140 performs fast and accurate face detection, which helps to define a rectangular region of interest including the face as the face region A. The near-face region B is then defined as the outer region close to face region A. The background layer C is defined as the outer region close to the near-face region B. There is no overlap between the three regions A, B, and C. In order to estimate the movement for purposes of the face liveness detection motion analysis, motion information is generated for these three ROIs between pairs of consecutive frames, as discussed below.

In completing the segmentation into regions of interest, three points deserve particular attention. First, the speed of face detection and the segmentation of all three regions of interests is a critical factor for real operational scenarios. Real time processing is required to prevent spoof attacks for real operational scenarios. Second, because the face location found by the face detection step helps define all three regions of interest, the accuracy of face detection is critical to determine regions of interest from the image to be used for the method. Motion information extracted from the wrong location can lead to failures of this spoof detection method. Third, the size of each region of interest also has an impact on the results of this method. Motion information needs to be extracted from and compared with appropriate regions of interest. Small sizes of each region may lead to less motion information or more noise, which can reduce the reliability and robustness of the method. Poorly sized regions may include too much noise to extract valid motion information.

Returning again to FIG. 4, at step 424 the (i+1)th frame is analyzed to determine $I_{i+1}(x, y, t)$ for each pixel in the (i+1)th image. At step 428, the determined $I_i(x, y, t)$ from step 416 and $I_{i+1}(x, y, t)$ from step 424 are compared to determine V for each pixel based on $I(\Delta x, \Delta y, \Delta t)$ for the image pair (e.g., to determine the difference between $I_{i+1}(x, y, t)$ and $I_i(x, y, t)$ for each pixel). The segment ROIs identified in step 420 and the determined V for each pixel for the image pair being analyzed are then input to step 432, which determines a motion feature $M_f(i)$ of the face region, a motion feature $M_o(i)$ of the outer face region, and a motion feature $M_b(i)$ of the background region.

The motion features determined in step 432 may be determined, for example, by concatenating all V for each pixel in the applicable ROI, although other mathematical methods for determining an overall vector from a collection of individual vectors may also be used. So the motion feature $M_f(i)$ is the vector of velocity of all pixels in the face region A; the motion feature $M_o(i)$ is the vector of velocity of all pixels in the near-face region B; the motion feature $M_b(i)$ is the vector of velocity of all pixels in the background region C. Motion features extracted in the background ROI are used as reference knowledge for comparing the other two regions.

Once motion features are extracted for the face region $(M_f)$, the near-face region $(M_o)$, and the background region $(M_b)$ in step 432, this information is provided to a trained classifier (which forms part of decision module 436) at step 440. Training of the classifier is discussed below. The trained classifier generates a determination about whether the input pair of frames shows enough evidence of being spoofed or live (i.e. the pair-decision) in step 444. In step 448, the counter i is incremented by one, and if the incremented i value is determined to be less than the total number of frames minus one in step 452, then the method returns to step 416 and is repeated for the next pair of frames. Thus, if the time-stamped frame sequence being analyzed contains N frames, there will be N−1 pair-decisions with respect to the spoofness or liveness of the sequence.

In the method 400, one pair-decision (D(i)) is made for each pair of consecutive frames. In real operational scenarios, frame sequences for a few seconds can contain up to several hundred frames. The method disclosed herein can help create an array of pair-decisions during this few seconds. Various algorithms may be used to combine these N−1 pair-decisions to make a final decision that could be more accurate and feasible in real operational scenarios. For example, the method 400 may use averaging or running averages to combine all pair-decisions and thus to help to increase the accuracy of the final decision of the face liveness detection system. Other mathematical methods of considering the N−1 pair-decisions to obtain a final decision may also be used with the scope of the present disclosure.

Another embodiment of the present disclosure will now be described with respect to FIGS. 5A, 5B, and 5C, which depict methods 500A, 500B, and 500C. The methods 500A, 500B, and 500C may be carried out in whole or in part by a face recognition device 100, or more particularly, by a processor 104 of a face recognition device 100. Additionally or alternatively, the methods 500A, 500B, and 500C may be carried out in whole or in part by a face detection or face matching module 170, 174 of a face recognition device 150 (which face detection or face matching module 170, 174 may comprise one or more processors).

Figure 5A:
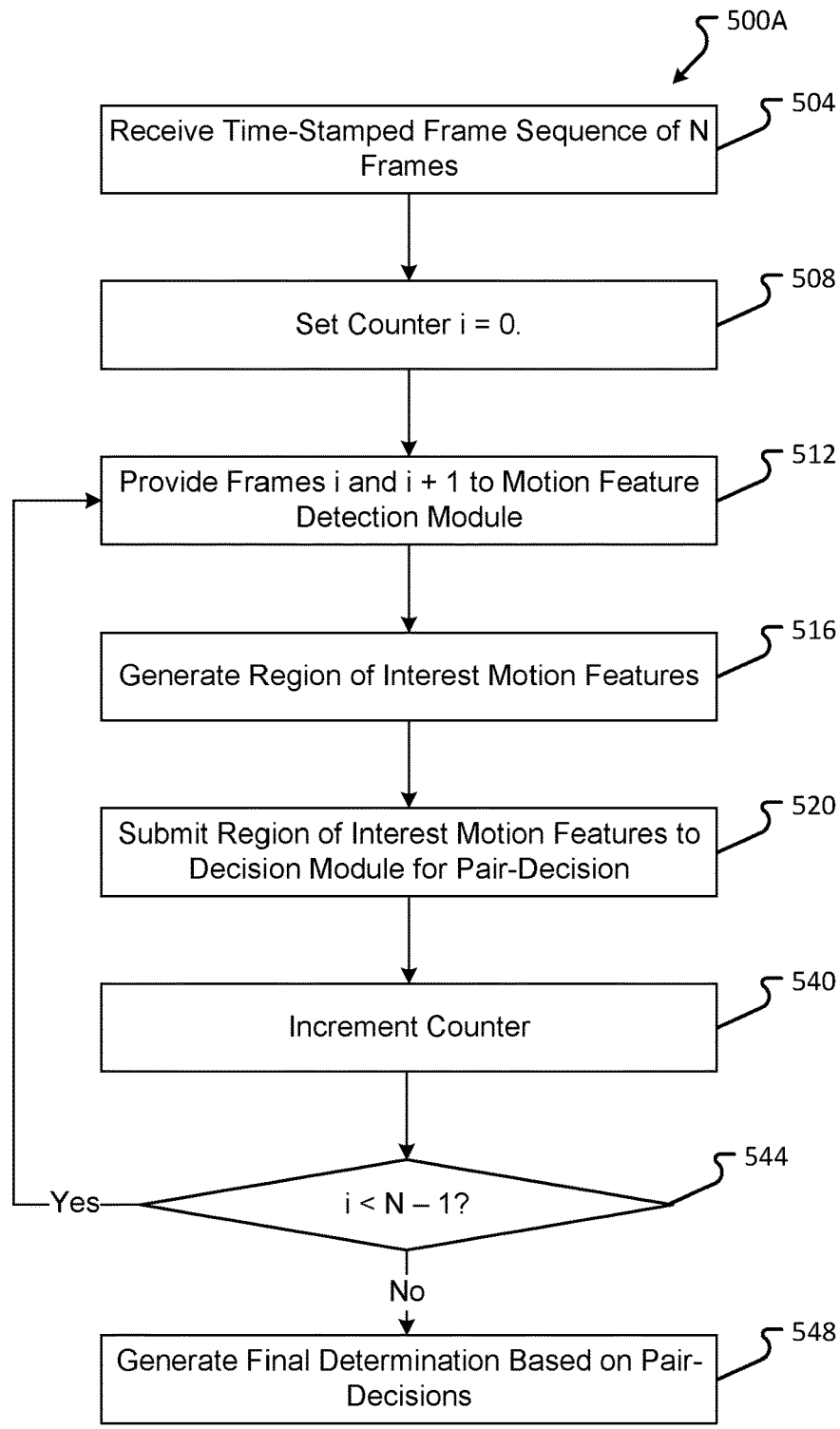
FIG. 5A is a flowchart of a face liveness detection method according to another embodiment of the present disclosure.

Referring first to FIG. 5A, the method 500A includes receiving a time-stamped frame sequence of N frames (step 504), where N is a positive integer. The time-stamped frame sequence may be received, for example, from an image capture device 108, or from another still camera or video camera. If the images are received from a still camera, then the images may be successive pictures taken by the still camera. If the images are received from a video camera, then the images may be individual frames of a short video sequence. The video sequence may, for example, be a 10-second video sequence, or a 5-second video sequence, or a 3-second video sequence, or a 2-second video sequence, or a 1-second video sequence. The frames may be extracted prior to receipt thereof, as in the method 500A, or the video sequence may be received as such, and the frames may be extracted from the video sequence upon receipt of the video sequence. In the method 500A, the individual frames of the time-stamped frame sequence are time-stamped prior to receipt thereof, although in some embodiments the frames may be time-stamped upon receipt, provided that the frames are provided in chronological order.

The method 500A further includes setting a counter i equal to zero (step 508). Because the method 500A involves generating a face liveness decision for each pair of chronological images in the time-stamped frame sequence, the counter i is used to ensure that all of the image pairs are analyzed, and also to ensure that once all of the image pairs are analyzed, a final face liveness determination is made.

In method 500A, the frames i and i+1 are provided to a motion feature detection module (step 512). (The operation of the motion feature detection module is discussed in greater detail below with respect to FIG. 5B.) The frames i and i+1 are sequential frames from the time-stamped frame sequence. For example, if a given time-stamped frame sequence comprises five frames, having sequential time stamps five hundredths of a second apart (e.g., with time stamps of 13:57:29.05, 13:57:29.10, 13:57:29.15, 13:57:29.20, and 13:57:29.25), then frames i and i+1 with i equal to zero would be the first two frames in the sequence (i.e. the frames with time stamps of 13:57:29.05 and 13:57:29.10).

The motion feature detection module returns information about the regions of interest (ROIs) in the frame pair as well as motion feature values for pixels in the frame pair. This information is utilized to generate region of interest motion features (step 516). The region of interest motion features include a motion feature $M_f(i)$ of the face region, a motion feature $M_o(i)$ of the outer face region, and a motion feature $M_b(i)$ of the background region. Because a pair of images is needed to determine the motion features (which, on a per-pixel level, represent the movement of a given pixel from one frame to the next, and on a region-of-interest level, represent the overall movement of a region of interest from one frame to the next), only one set of region of interest motion features is generated for each frame pair i, i+1.

The region of interest motion features are submitted to the decision module to obtain a pair-decision (step 520). (The operation of the decision module is discussed in greater detail below with respect to FIG. 5C.) The decision module generates the pair-decision based on comparison of the region of interest motion features, using information about known live face and known spoof face image sequences. As explained previously, if the region of interest motion features are highly correlated, then the decision module will generate a spoofed face determination, while if the region of interest motion features are not correlated, then the decision module will generate a live face determination. Machine learning techniques are used to learn the correlation and make this determination.

The counter i is incremented at step 540, and then compared to N+1 in step 544. If i is less than N-1, then the method 500A returns to step 512, where the next pair of frames i and i+1 are provided to the motion feature detection module. If i is not less than N-1, then all of the consecutive frame pairs within the time-stamped frame sequence have been analyzed, and the method 500A continues to step 548.

In step 548, a final face liveness determination is generated based on the pair-decisions resulting from the step(s) 520. The N-1 pair-decisions may be combined using various algorithms to make a final decision that, in real operational scenarios, may be more accurate than a decision based only on one pair decision. For example, the average decision might be used, or the majority decision. Other algorithms may also be used to make a final face liveness determination.

Figure 5B:
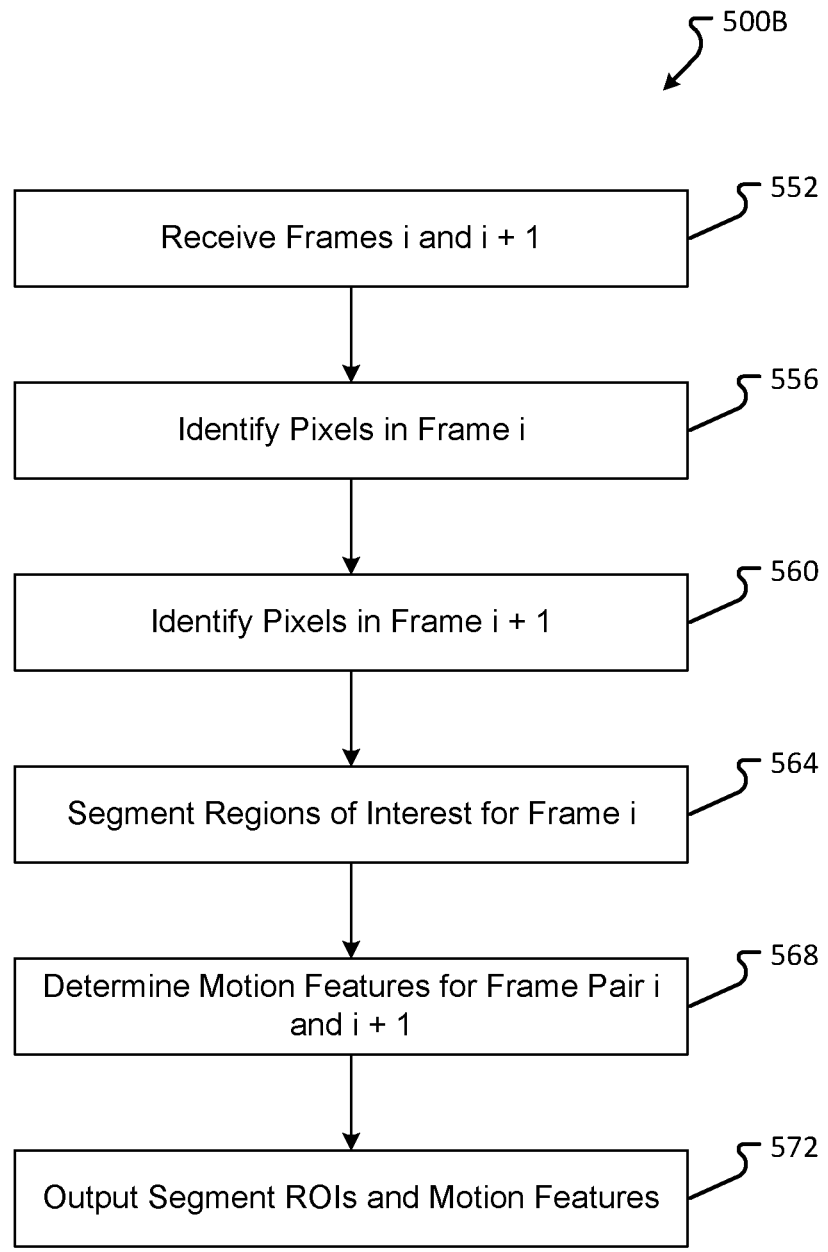
FIG. 5B is a flowchart of a portion of a face liveness detection method according to yet another embodiment of the present disclosure.

A method 500B of operating a motion feature detection module is described in FIG. 5B. In the method 500B, the motion feature detection module receives frames i and i+1 (step 552). The motion feature detection module analyzes each image, identifying all pixels in frame i (step 556) and corresponding pixels in frame i+1 (step 560). The motion feature detection module also segments the regions of interest for frame i, by identifying the face region of interest A, the near-face region of interest B, and the background region of interest C as identified in FIG. 6. Locations of these three regions of interest are applied to frame i+1 as well for future reference.

In step 568, the motion feature detection module determines the motion feature M for each identified pixel of the frame i and corresponding pixel for the frame i+1. By identifying a magnitude of a change in position of the pixel in question (e.g. x, y) over a known change in time (determined using the time stamps on the frames), the motion feature (including magnitude and direction) for each analyzed pixel can be determined.

In step 572, the motion feature module outputs the segmented regions of interest of step 564, and further outputs the motion features determined in step 568. Only motion features from segmented regions of interest are kept for future decision-making. The output information may then be used (for example, as described with respect to FIG. 5A) to make a face liveness determination for a time-stamped frame sequence.

Figure 5C:
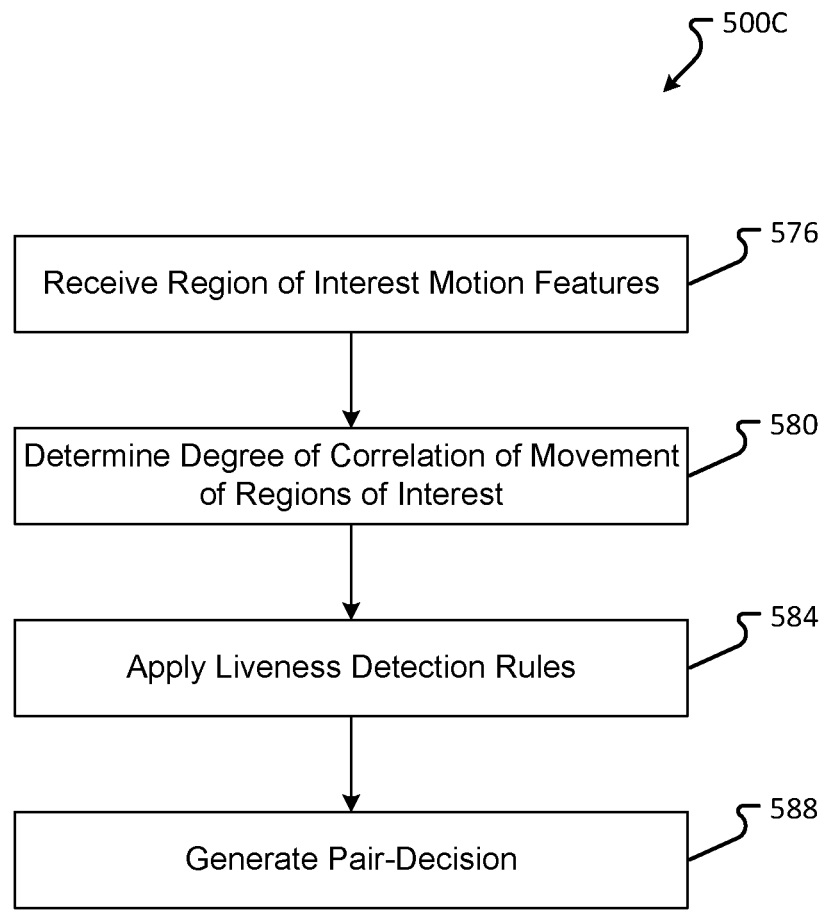
FIG. 5C is a flowchart of a portion of a face liveness detection method according to still another embodiment of the present disclosure.

Turning now to FIG. 5C, a method 500C of operating a decision module commences with the receipt by the decision module of region of interest motion features (step 576). These region of interest motion features represent the motion of each region of interest (face, near-face, and background) from one frame to the next. Based at least in part on the motion features, the decision module determines a degree of correlation of the movement of each region of interest (step 580). For example, the decision module may determine whether the background moved in the same or a similar direction as the face, whether the near-face region moved in the same or a similar direction as the face and/or as the background, and/or whether the background moved all.

The decision module may apply previously formulated face liveness detection rules to the determined correlations between or among motion features (step 584). The previously formulated face liveness detection rules may comprise rules formulated by a face recognition device 100 or 150 during a training session or method, as described with respect to FIGS. 7A-8C below, in which face liveness of the provided time-stamped image frame sequences is known. Alternatively, the previously formulated face liveness detection rules may comprise rules provided to the face recognition device 100 or 150 after formulation of the same using a different face recognition device and known live and spoofed images.

The decision module generates a pair decision at step 588. The pair-decision may be a binary face liveness determination (e.g. binary or spoofed), or it may be or represent a probability of face liveness (e.g. 60% likelihood that face is live), or it may be a determination paired with a certainty that the determination is correct (e.g. spoofed face, 54% certainty), or it may be a number on a scale, where one end of the scale represents 100% certainty of a live face and the other end of the scale represents 100% certainty of a spoofed face. The pair-decision may also be provided in any other desired format.

The methods 400 and 500A, 500B, and 500C as described above are not mutually exclusive. Aspects of the method 400 may be incorporated into or otherwise used in the method 500A, 500B, and/or 500C, and aspects of the methods 500A, 500B, and/or 500C may be incorporated into or otherwise used in the method 400.

Figure 7A:
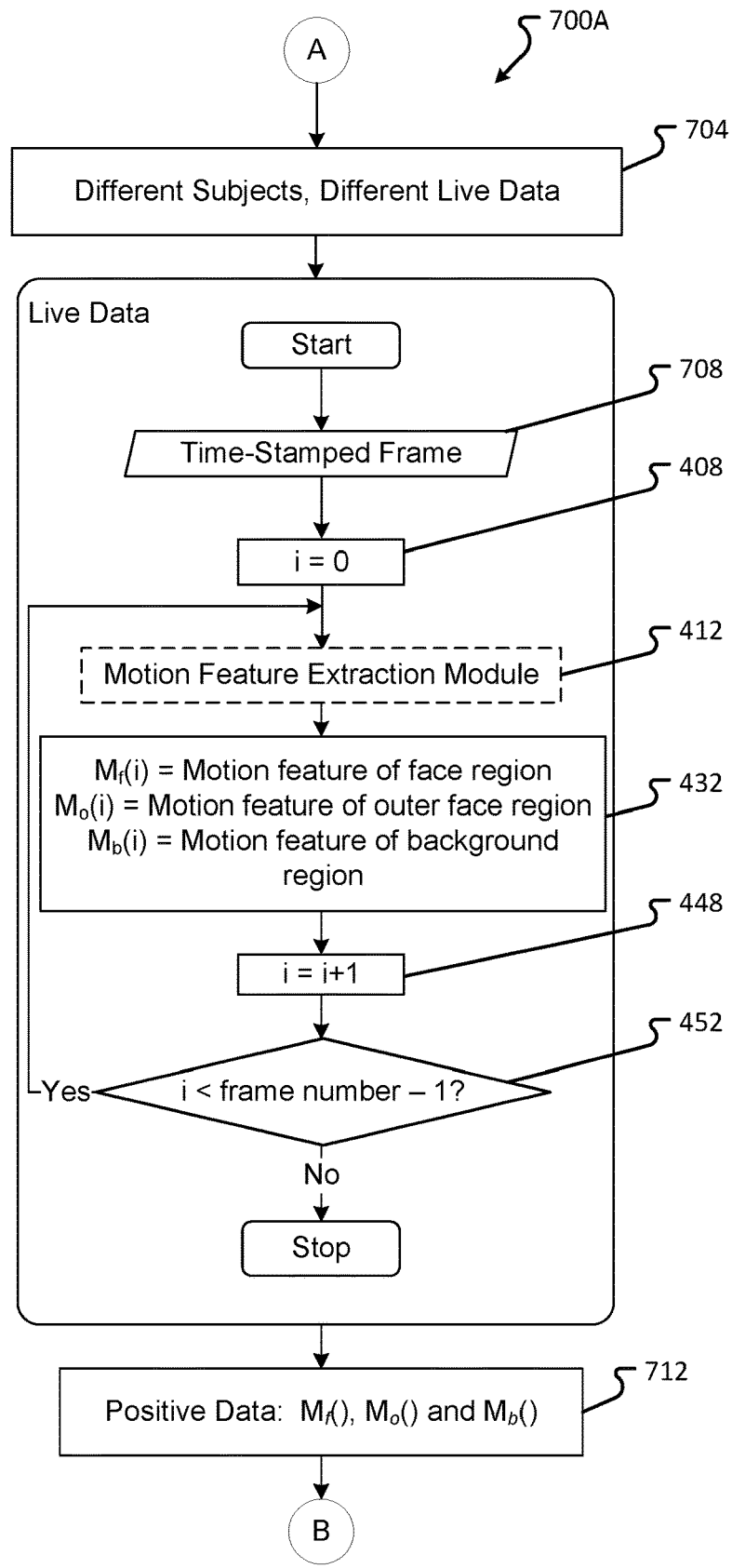
FIG. 7A is a flowchart of a portion of a training process for a face liveness detection method according to an embodiment of the present disclosure.
Figure 7B:
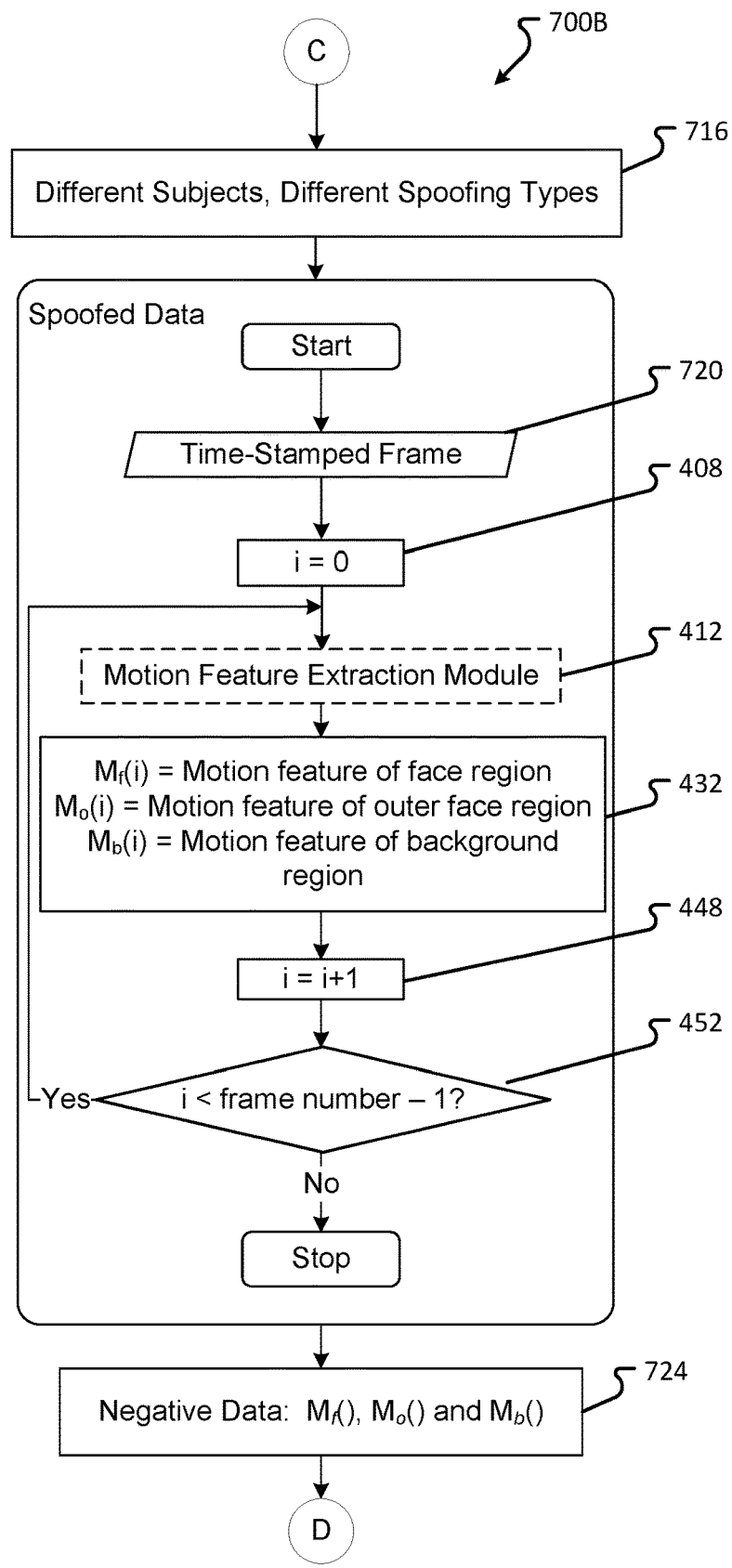
FIG. 7B is a flowchart of another portion of the training process for a face liveness detection method according to the embodiment of FIG. 7A.
Figure 7C:
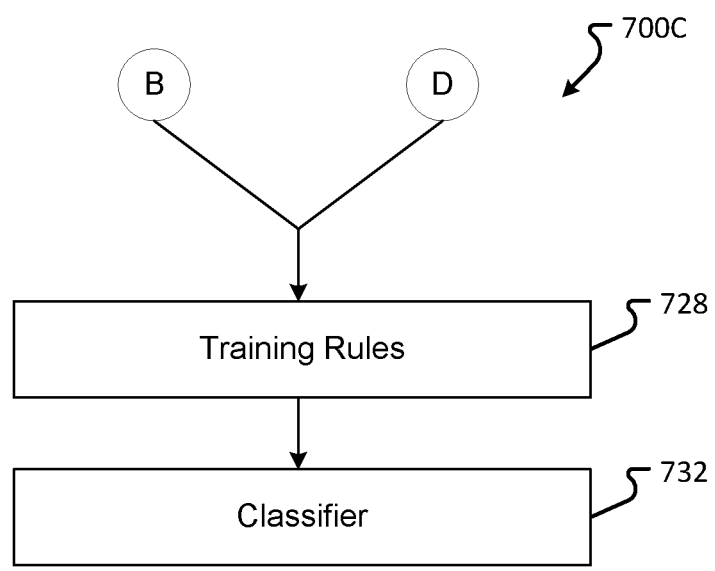
FIG. 7C is a flowchart of yet another portion of the training process for a face liveness detection method according to the embodiment of FIG. 7A.

FIGS. 7A, 7B, and 7C illustrate portions 700A, 700B, and 700C, respectively, of a training method 700 for a classifier (e.g., the portion of a face detection unit 140 that makes face liveness determinations). Generally speaking, in the training method 700 motion features for the three ROIs can be measured and characterized across multiple spoofed and live scenarios to determine normality, where a "positive" result corresponds to a live face, and a "negative" result corresponds to a "spoofed" face. This data can then be used to develop training rules for input into a classifier, so that the classifier can accurately distinguish between live and spoofed faces. A Bayesian model can be used to train the classifier, although other machine learning methods, like neural network techniques, can be utilized as well. The classifier can be part of the face detection unit or the face matching unit; it also can combine motion feature detection module into a unique and separate unit.

A large amount of ground truth data is collected and used to train the classifier. Thus, in FIG. 7A, the training method 700 commences with the collection of various time-stamped frame sequences containing different subjects and different live data at step 704. Different subjects are acquired using several different cameras to collect live face frame sequences in different scenarios of no movement, slight movement and large amount of movement. This live data is then input into a face recognition device 100 or 150 (which may, for the purpose of training, be placed in a training mode or otherwise configured to all or part of the method 700). The time-stamped frame sequences 708 (each containing data regarding live, non-spoofed faces) are then processed through steps 408 through 432 (including steps 416, 420, 424, and 428, of which motion feature extraction module 412 is comprised), as described above with respect to FIG. 4. Once the motion features $M_f(i)$, $M_o(i)$, and $M_b(i)$ are determined, however, the method 700A passes directly to steps 448 and 452 (skipping steps 440 and 444 of the decision module 436 because the training method 700 is intended to train the classifier rather than obtain a face liveness determination from the classifier). Steps 448 and 452 are described above with respect to FIG. 4.

Once the determination at step 452 is "no," the frame-pair specific motion features $M_f(i)$, $M_o(i)$, and $M_b(i)$ may be grouped, averaged, compiled, combined, or otherwise considered to develop a final positive data set for the time-stamped frame sequence in question that includes motion features $M_f$, $M_o$, and $M_b$ for all training samples in a pair (step 712). As shown in FIG. 7C, this positive data set is then used to generate one or more training rules in step 728, which are provided to the classifier in step 732. As noted above, a processor such as the processor 104 may use a Bayesian model to analyze the data provided from the methods 700A and 700B and develop training rules in step 728, although other machine learning methods, like neural network techniques, can be utilized as well.

Additionally, once a set of training rules is determined, that set of training rules may be provided to the face recognition system 100 or 150 or another face recognition system, so that the receiving face recognition system need not be trained. In some embodiments, however, the training may be fully or partially system-specific (e.g. because the background in images obtained by facial recognition systems installed in different places will likely be different), such that training rules developed using one system cannot be simply transferred over to a different face recognition system.

FIG. 7B shows the portion of training method 700 that involves, at step 716, collection of various time-stamped frame sequences containing different subjects and different spoofing types. The spoofing types are based on the live data collected at step 704, which is used to generate different type of spoofing frame sequences via different spoofing media. This spoofing data is then input into the same face recognition device 100 or 150 as discussed with respect to FIG. 7A (which, as mentioned in connected with FIG. 7A, may, for the purpose of training, be placed in a training mode or otherwise configured to all or part of the method 700). The time-stamped frame sequences 720 (each containing data regarding spoofed faces) are then processed through steps 408 through 432 (including steps 416, 420, 424, and 428, of which motion feature extraction module 412 is comprised), as described above with respect to FIG. 4. Once the motion features $M_f(i)$, $M_o(i)$, and $M_b(i)$ are determined for a given frame sequence, however, the method 700B passes directly to steps 448 and 452 (skipping steps 440 and 444 of the decision module 436 because the training method 700 is intended to train the classifier rather than obtain a face liveness determination from the classifier). Steps 448 and 452 are described above with respect to FIG. 4. Once the determination at step 452 is "no," the frame-pair specific motion features $M_f(i)$, $M_o(i)$, and $M_b(i)$ may be grouped, averaged, compiled, combined, or otherwise considered to develop a final negative data set for the time-stamped frame sequence in question in step 724, with the final negative data set including motion features $M_f$, $M_o$, and $M_b$ corresponding to the spoofed frame sequence in question. As shown in FIG. 7C, this negative data set is then used (together with the positive data set generated by the method 700A) to generate one or more training rules in step 728 (as described above), which training rules are provided to the classifier in step 732.

As evident from the above description, in the training method 700, live frame sequences are used to generate positive data while spoofed frame sequences are used to generate negative data. Both positive and negative data contain motion features from various regions of interest. After training, the target classifier can be used to differentiate spoof and live.

Figure 8A:
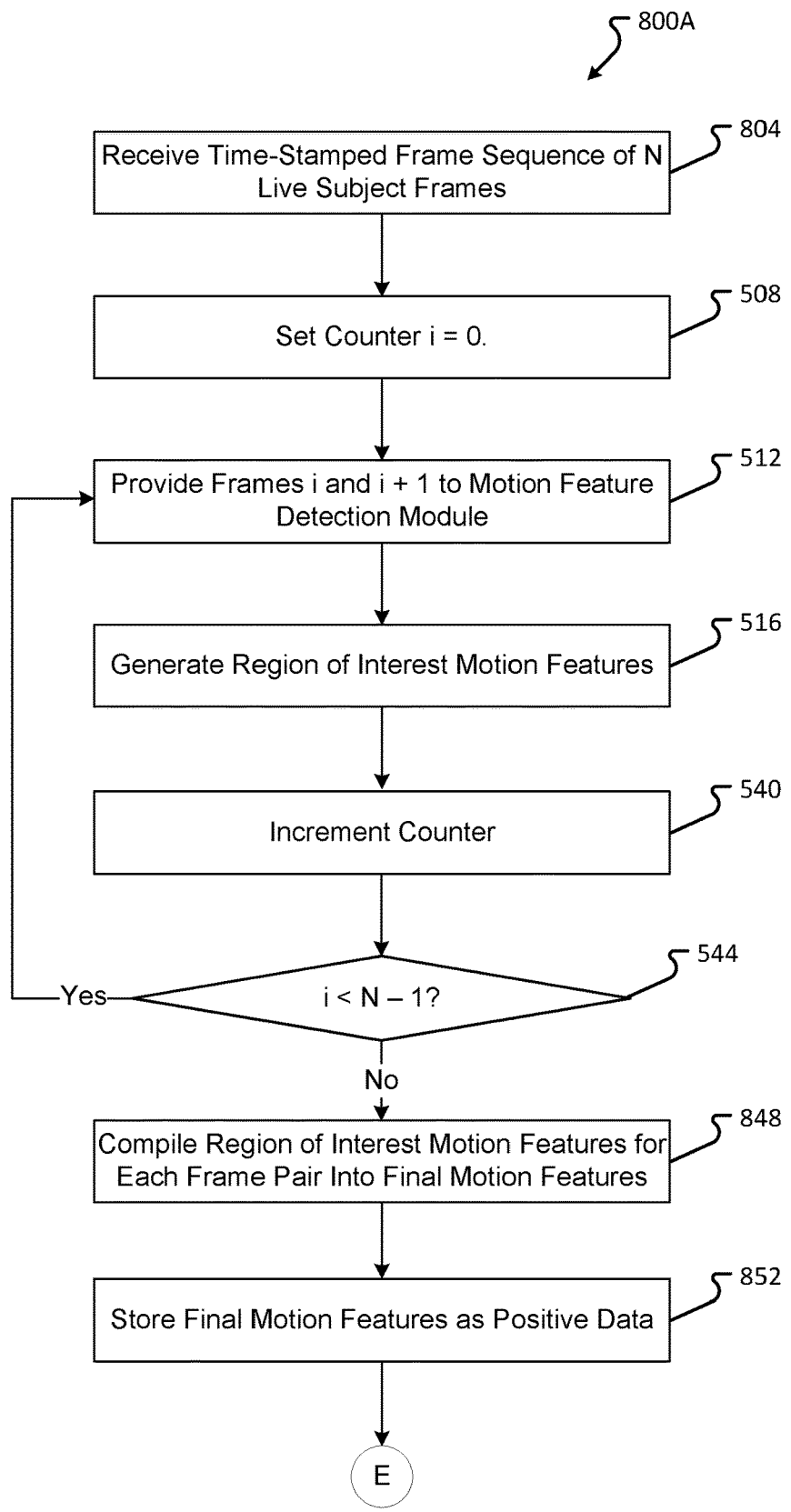
FIG. 8A is a flowchart of a portion of a training process for a face liveness detection method according to another embodiment of the present disclosure.
Figure 8B:
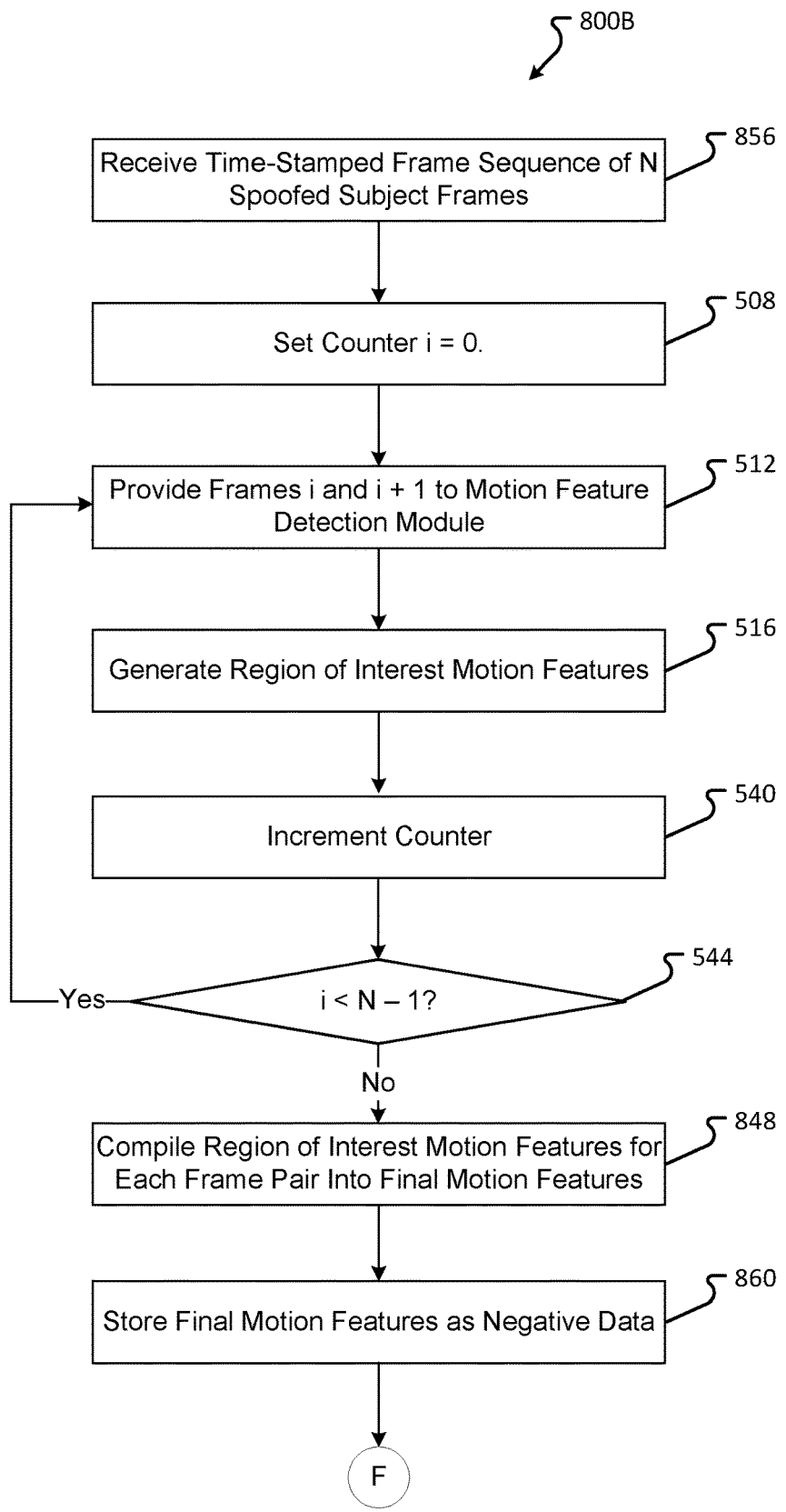
FIG. 8B is a flowchart of another portion of the training process for a face liveness detection method according to the embodiment of FIG. 8A.
Figure 8C:
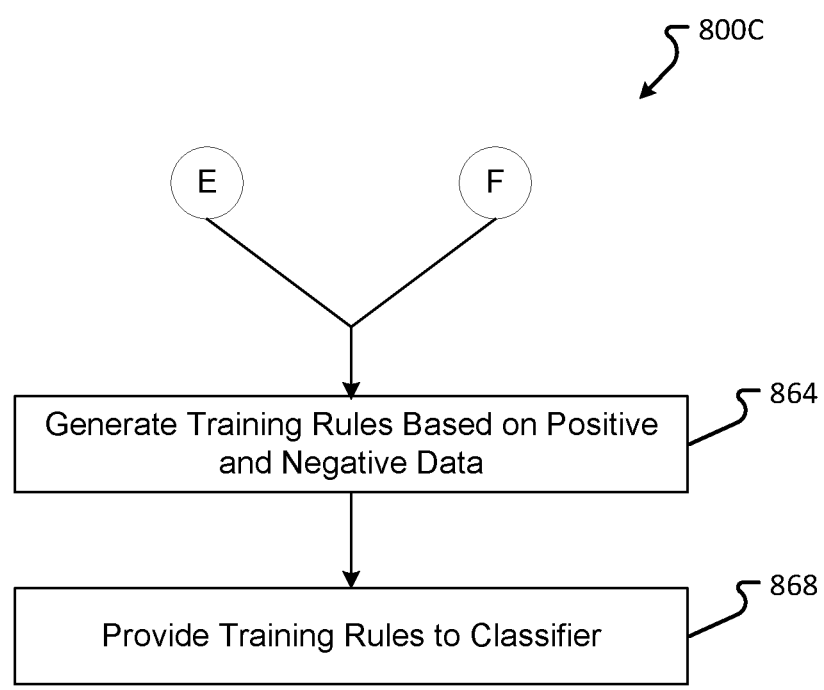
FIG. 8C is a flowchart of yet another portion of the training process for a face liveness detection method according to the embodiment of FIG. 8A.

FIGS. 8A, 8B, and 8C depict portions 800A, 800B, and 800C of a method 800 for training a classifier according to another embodiment of the present disclosure. Generally speaking, the training method 800 comprises completing portions of a face liveness detection method such as the face liveness detection method 500 with known live data and known spoofed data, then correlating the results of the portions of the face liveness detection method with known face liveness result (e.g. live face or spoofed face) and creating rules based on those correlations. The method may be carried out by one or more processors (such as, for example, the processor 104) or modules (such as, for example, the modules of the face recognition device 150).

More specifically, and with reference to FIG. 8A, the method 800 comprises receiving a time-stamped frame sequence of N known live-subject frames (step 804), where N is a positive integer. As with step 504 of the method 500A, the time-stamped frame sequence may be received, for example, from an image capture device 108, or from another still camera or video camera. If the images are received from a still camera, then the images may be successive pictures taken by the still camera. If the images are received from a video camera, then the images may be individual frames of a short video sequence. The video sequence may, for example, be a 10-second video sequence, or a 5-second video sequence, or a 3-second video sequence, or a 2-second video sequence, or a 1-second video sequence. The frames may be extracted prior to receipt thereof, as in the method 800 depicted in FIG. 8A, or the video sequence may be received as such, and the frames may be extracted from the video sequence upon receipt of the video sequence. In the method 800, the individual frames of the time-stamped frame sequence are time-stamped prior to receipt thereof, although in some embodiments the frames may be time-stamped upon receipt, provided that the frames are provided in chronological order.

The method 800 also comprises a number of steps described above with respect to the method 500A, including steps 508, 512, 516, 540, and 544. If the determination at step 544 is that i is not less than N−1, then the method 800 continues to step 848, where region of interest motion features $M_f(i)$, $M_o(i)$, and $M_b(i)$ generated at step 516 for each frame pair i, i+1 are compiled into final motion features $M_f$, $M_o$, and $M_b$. These final motion features $M_f$, $M_o$, and $M_b$ are then stored as positive data (step 852), meaning that the final motion features are stored as indicative of a live face.

Referring now to FIG. 8B, the method 800 also comprises receiving a time-stamped frame sequence of N known spoofed-subject frames (step 856), where N is a positive integer. Other than the subject matter of the frame sequence being a spoofed subject rather than a live subject, the step 856 may be the same as or similar to the step 804.

Steps 508, 512, 516, 540, and 544 are repeated for the time-stamped frame sequence of N spoofed-subject frames. When, at step 544, i is not less than N−1, then the method 800 continues to step 848, where region of interest motion features $M_f(i)$, $M_o(i)$, and $M_b(i)$ generated at step 516 for each frame pair i, i+1 of the spoofed-subject frame sequence are compiled into final motion features $M_f$, $M_o$, and $M_b$. These final motion features $M_f$, $M_o$, and $M_b$ are then stored as positive data (step 860), meaning that the final motion features are stored as indicative of a spoofed face.

Referring now to FIG. 8C, the stored positive data from the portion 800A of the method 800, and the stored negative data from the portion 800B of the method 800, are utilized to generate training rules (step 864). In particular, one or more processors (such as the processor 104) may compare the positive and negative data to determine unique similarities among and/or features of the positive data, unique similarities among and/or features of the negative data, and differences between the positive and negative data. These unique similarities, features and differences may then be converted into rules that may be used to classify new data sets as corresponding to a live face or a spoofed face. For example, if a new data set shares a unique similarity or feature with the positive data set, then it may be classified as a live face, while if the new data set shares a unique similarity or feature with a negative data set, then it may be classified as a spoofed face.

Once the training rules are generated, they may be provided to a classifier (step 868), thus enabling the classifier to make face liveness determinations. The classifier may or may not be associated with the face recognition system, device or module (or other system, device, processor, or module) that executed the method 800. In other words, the method 800 may be executed by one face recognition system, device or module or other system, device, processor, or module, and the resulting rules may be provided to unrelated face recognition systems, devices, or modules. In some embodiments, however, some or all of the generated rules may be specific to a particular face recognition system, device, or module (perhaps due to the unique background in frame sequences captured by and/or provided to the face recognition system, device, or module), such that the rules are not suitable for use by another face recognition system, device, or module.

The methods 700 and 800 as described above are not mutually exclusive. Aspects of the method 700 may be incorporated into or otherwise used in the method 800, and aspects of the method 800 may be incorporated into or otherwise used in the method 700.

The passive face liveness detection methods described herein may be utilized among different spoofing scenarios as long as the acquisition camera is reasonably fixed. These methods do not require cooperation between the subject and the detection system. The method can be implemented in a module that can be installed on or otherwise provided to any current standard face recognition system or face enrollment system that provides a capability for anti-spoofing, without interrupting or changing the framework of the existing system.

Exemplary aspects are directed toward:
A method of determining face liveness, comprising:
receiving, at a processor of a face recognition system and from an image capture device of the face recognition system, a time-stamped frame sequence;
identifying corresponding pixels for each pair of sequential frames in the time-stamped frame sequence;
segmenting one of each pair of sequential frames in the time-stamped frame sequence into regions of interest;
calculating a motion feature for each region of interest of each pair of sequential frames in the time-stamped frame sequence;
generating a preliminary face-liveness determination for each pair of sequential frames in the time-stamped frame sequence, based on a comparison of the calculated motion features for each region of interest of the pair of sequential frames; and
making a final face-liveness determination based on the generated preliminary face liveness determinations.

Any of the above aspects, wherein the time-stamped frame sequence comprise a series of photographs taken by the image capture device.

Any of the above aspects, wherein the regions of interest comprise a face region, a near-face region, and a background region.

Any of the above aspects, wherein the motion feature is calculated based on estimated pixel velocities.

Any of the above aspects, wherein the final face-liveness determination is made by averaging the preliminary face liveness determinations.

Any of the above aspects, wherein the final face-liveness determination matches a majority of preliminary face liveness determinations.

Any of the above aspects, wherein the preliminary face-liveness determination for each pair of sequential frames in the time-stamped frame sequence is further based on liveness detection rules stored in a memory of the face recognition system.

Any of the above aspects, wherein the liveness detection rules comprise rules configured to detect artificial patterns in the calculated motion features.

A method of training a classifier of a face recognition system, comprising:
receiving, at a processor of a face recognition system and from an image capture device associated with the face recognition system, a first plurality of time-stamped frame sequences having a live subject, and a second plurality of time-stamped frame sequences having a spoofed subject;

for each of the time-stamped frame sequences in the first and second pluralities of time-stamped frame sequences:
identifying corresponding pixels for each pair of sequential frames in the time-stamped frame sequence;
segmenting one of each pair of sequential frames in the time-stamped frame sequence into regions of interest; and
calculating a motion feature for each region of interest of each pair of sequential frames in the time-stamped frame sequence;
storing the calculated motion features for each time-stamped frame sequence from the first plurality of time-stamped frame sequences as positive data, and storing the calculated motion features for each time-stamped frame sequence from the second plurality of time-stamped frame sequences as negative data; and
generating training rules based on the positive and negative data.

Any of the above aspects, wherein at least one of the time-stamped frame sequences comprises a series of photographs taken by the image capture device or a series of frames from a video recorded by the image capture device.

Any of the above aspects, wherein the regions of interest comprise a face region, a near-face region, and a background region.

Any of the above aspects, further comprising estimating a pixel velocity for each pixel within each region of interest, and further wherein the estimated pixel velocities are used to calculate the motion feature for each region of interest.

Any of the above aspects, wherein the spoofed subject of at least one of the second plurality of time-stamped frame sequences is a printed photo spoof, a shaped board spoof, a printed paper spoof, a displayed static digital image spoof, or a smart phone replay video spoof.

Any of the above aspects, wherein the spoofed subjects of the second plurality of time-stamped frame sequences comprise different types of spoofs.

Any of the above aspects, wherein machine learning techniques are used to generate the training rules based on the positive and negative data.

A face recognition system comprising:
an image capture device;
a processor;
a face detection unit comprising a memory; and
a face matching unit;
wherein the memory stores instructions that, when executed by the processor, cause the processor to:
receive, from the image capture device, a time-stamped frame sequence; identify corresponding pixels for each pair of sequential frames in the time-stamped frame sequence;
segment one of each pair of sequential frames in the time-stamped frame sequence into regions of interest;
calculate a motion feature for each region of interest of each pair of sequential frames in the time-stamped frame sequence;
generate a preliminary face-liveness determination for each pair of sequential frames in the time-stamped frame sequence, based on a comparison of the calculated motion features for the pair of sequential frames; and
make a final face-liveness determination based on the generated preliminary face liveness determinations.

Any of the above aspects, wherein the memory stores additional instructions that, when executed by the processor, further cause the processor to estimate a pixel velocity for each pixel within each region of interest, and further wherein the estimated pixel velocities are used to calculate the motion feature for each region of interest.

Any of the above aspects, wherein the regions of interest comprise a face region, a near-face region, and a background region.

Any of the above aspects, wherein the memory stores additional instructions that, when executed by the processor, further cause the processor to provide a face associated with the time-stamped frame sequence to the face matching unit when the final face liveness determination indicates that the face is live.

Any of the above aspects, wherein the face matching unit comprises a second memory, the second memory storing second instructions that, when executed by the processor, cause the processor to compare a face associated with the time-stamped frame sequence to a plurality of stored faces to identify a matching face.

Any one or more of the aspects as substantially described herein.

One or more means adapted to perform any one or more of the above aspects.

A non-transitory computer readable information storage media that stores instructions for performing any one or more of the above aspects.

For purposes of explanation, numerous details are set forth in order to provide a thorough understanding of the present embodiments. It should be appreciated however that the techniques herein may be practiced in a variety of ways beyond the specific details set forth herein.

Furthermore, while the exemplary embodiments illustrated herein may show the various components of the system collocated, it is to be appreciated that the various components of the system can be located at distant portions of a distributed network, such as a communications network and/or the Internet, or within a dedicated secure, unsecured and/or encrypted system. Thus, it should be appreciated that the components of the system can be combined into one or more devices, or collocated on a particular node/element(s) of a distributed network, such as a communications network. As will be appreciated from the description, and for reasons of computational efficiency, the components of the system can be arranged at any location within a distributed network without affecting the operation of the system.

Furthermore, it should be appreciated that the various links, including communications channel(s), connecting the elements (which may not be not shown) can be wired or wireless links, or any combination thereof, or any other known or later developed element(s) that is/are capable of supplying and/or communicating data and/or signals to and from the connected elements. The term module as used herein can refer to any known or later developed hardware, software, firmware, or combination thereof that is capable of performing the functionality associated with that element. The terms determine, calculate and compute, and variations thereof, as used herein are used interchangeably and include any type of methodology, process, mathematical operation or technique.

While the above-described flowcharts/operational flows have been discussed in relation to a particular exemplary sequence of events, it should be appreciated that changes to this sequence can occur without materially effecting the operation of the embodiment(s). Additionally, the exact sequence of events need not occur as set forth in the exemplary embodiments, but rather the steps can be performed by one or the other device(s) in the system. Additionally, the exemplary techniques illustrated herein are not limited to the specifically illustrated embodiments but can also be utilized with the other exemplary embodiments and each described feature is individually and separately claimable.

As will be appreciated by one skilled in the art, aspects of the present disclosure may be embodied as a system, method, and/or computer program product. Thus, aspects of the present disclosure may be embodied entirely in hardware, entirely in software (including, but not limited to, firmware, program code, resident software, microcode), or in a combination of hardware and software. All such embodiments may generally be referred to herein as a circuit, a module, or a system. In addition, aspects of the present invention may be in the form of a computer program product embodied in one or more computer readable media having computer readable program code embodied thereon.

A computer readable medium as described herein may be a computer readable storage medium, examples of which include, but are not limited to, an electronic, magnetic, optical, electromagnetic, infrared, or semiconductor system, apparatus, or device, or any suitable combination thereof. As used herein, a computer readable storage medium may be any non-transitory, tangible medium that can contain or store a program for use by or in connection with an instruction execution system, apparatus, device, computer, computing system, computer system, or any programmable machine or device that inputs, processes, and outputs instructions, commands, or data. A non-exhaustive list of specific examples of a computer readable storage medium include an electrical connection having one or more wires, a portable computer diskette, a floppy disk, a hard disk, a random access memory (RAM), a read-only memory (ROM), a USB flash drive, an non-volatile RAM (NVRAM or NOVRAM), an erasable programmable read-only memory (EPROM or Flash memory), a flash memory card, an electrically erasable programmable read-only memory (EEPROM), an optical fiber, a portable compact disc read-only memory (CD-ROM), a DVD-ROM, an optical storage device, a magnetic storage device, or any suitable combination thereof. A computer readable storage medium can be any computer readable medium that is not a computer readable signal medium such as a propagated data signal with computer readable program code embodied therein.

Program code may be embodied as computer-readable instructions stored on or in a computer readable storage medium as, for example, source code, object code, interpretive code, executable code, or combinations thereof. Any standard or proprietary, programming or interpretive language can be used to produce the computer-executable instructions. Examples of such languages include C, C++, C#, Pascal, JAVA, JAVA Script, BASIC, Smalltalk, Visual Basic, and Visual C++.

Transmission of program code embodied on a computer readable medium can occur using any appropriate medium including, but not limited to, wireless, wired, optical fiber cable, radio frequency (RF), or any suitable combination thereof.

The program code may execute entirely on a user's/operator's/administrator's computer, partly on such a computer, as a stand-alone software package, partly on the user's/operator's/administrator's computer and partly on a remote computer, or entirely on a remote computer or server. Any such remote computer may be connected to the user's/operator's/administrator's computer through any type of network, including a local area network (LAN) or a wide area network (WAN), or the connection may be made to an external computer (for example, through the Internet using an Internet Service Provider).

Additionally, the systems, methods and protocols described herein can be implemented to improve one or more of a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device such as PLD, PLA, FPGA, PAL, any comparable means, or the like. In general, any device capable of implementing a state machine that is in turn capable of implementing the methodology illustrated herein can benefit from the various communication methods, protocols and techniques according to the disclosure provided herein.

Examples of the processors as described herein include, but are not limited to, at least one of Qualcomm® Snapdragon® 800 and 801, Qualcomm® Snapdragon® 610 and 615 with 4G LTE Integration and 64-bit computing, Apple® A7, A8, A8X, A9, A9X, or A10 processors with 64-bit architecture, Apple® M7, M8, M9, or M10 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, Broadcom® AirForce BCM4704/BCM4703 wireless networking processors, the AR7100 Wireless Network Processing Unit, other industry-equivalent processors, and may perform computational functions using any known or future-developed standard, instruction set, libraries, and/or architecture.

Furthermore, the disclosed methods may be readily implemented in software using object or object-oriented software development environments that provide portable source code that can be used on a variety of computer, workstation or mobile device platforms. Alternatively, the disclosed system may be implemented partially in hardware using standard logic circuits or a VLSI design. Whether software or hardware is used to implement the systems in accordance with this invention is dependent on the speed and/or efficiency requirements of the system, the particular function, and the particular software or hardware systems or microprocessor or microcomputer systems being utilized. The methods illustrated herein however can be readily implemented in hardware and/or software using any known or later developed systems or structures, devices and/or software by those of ordinary skill in the applicable art from the functional description provided herein and with a general basic knowledge of the computer and image processing arts.

Moreover, the disclosed methods may be readily implemented in software executed on programmed general-purpose computer, a special purpose computer, mobile device, smartphone, a microprocessor, or the like. In these instances, the systems and methods of this invention can be implemented as program embedded on personal computer such as JAVA® or CGI script, as a resource residing on a server or graphics workstation, as a routine embedded in a dedicated fingerprint processing system, as a plug-in, or the like. The system can also be implemented by physically incorporating the system and method into a software and/or hardware system, such as the hardware and software systems of an image processor.

While this invention has been described in conjunction with a number of embodiments, it is evident that many alternatives, modifications and variations would be or are apparent to those of ordinary skill in the applicable arts. Accordingly, it is intended to embrace all such alternatives, modifications, equivalents, and variations that are within the spirit and scope of this disclosure.

The invention claimed is:

1. A method of determining face liveness, comprising:
   receiving, at a processor of a face recognition system and from an image capture device of the face recognition system, a time-stamped frame sequence;
   identifying corresponding pixels for each pair of sequential frames in the time-stamped frame sequence;
   adjusting overall intensity of each successive image;
   segmenting one of each pair of sequential frames in the time-stamped frame sequence into regions of interest;
   calculating a motion feature for each region of interest of each pair of sequential frames in the time-stamped frame sequence, the motion feature at least based on a change in position of a pixel between a pair of sequential frames over a known change in time determined from data within time-stamps of the time-stamped fame sequence;
   generating a preliminary face-liveness determination for each pair of sequential frames in the time-stamped frame sequence, based on a comparison of the calculated motion features for each region of interest of the pair of sequential frames; and
   making a final face-liveness determination based on the generated preliminary face liveness determinations, wherein one or more thresholds for either face-liveness determination are adjusted based on a frame rate at which the time-stamped frame sequence is taken.

2. The method of claim 1, wherein the time-stamped frame sequence comprise a series of photographs taken by the image capture device.

3. The method of claim 1, wherein the regions of interest comprise a face region, a near-face region, and a background region.

4. The method of claim 1, wherein the motion feature is calculated based on estimated pixel velocities.

5. The method of claim 1, wherein the final face-liveness determination is made by averaging the preliminary face liveness determinations.

6. The method of claim 1, wherein the final face-liveness determination matches a majority of preliminary face liveness determinations.

7. The method of claim 1, wherein the preliminary face-liveness determination for each pair of sequential frames in the time-stamped frame sequence is further based on liveness detection rules stored in a memory of the face recognition system.

8. The method of claim 7, wherein the liveness detection rules comprise rules configured to detect artificial patterns in the calculated motion features.

9. A method of training a classifier of a face recognition system, comprising:
   receiving, at a processor of a face recognition system and from an image capture device associated with the face recognition system, a first plurality of time-stamped frame sequences having a live subject, and a second plurality of time-stamped frame sequences having a spoofed subject;
   for each of the time-stamped frame sequences in the first and second pluralities of time-stamped frame sequences:
      identifying corresponding pixels for each pair of sequential frames in the time-stamped frame sequence;
      adjusting overall intensity of each successive image;
      segmenting one of each pair of sequential frames in the time-stamped frame sequence into regions of interest; and
      calculating a motion feature for each region of interest of each pair of sequential frames in the time-stamped frame sequence, the motion feature at least based on a change in position of a pixel between a pair of sequential frames over a known change in time determined from data within time-stamps of the time-stamped fame sequence;
   storing the calculated motion features for each time-stamped frame sequence from the first plurality of time-stamped frame sequences as positive data, and storing the calculated motion features for each time-stamped frame sequence from the second plurality of time-stamped frame sequences as negative data;
   generating training rules for the classifier of the face recognition system based on the positive and negative data; and
   adjusting one or move thresholds for a face-liveness determination based on a frame rate at which the time-stamped frame sequence is taken.

10. The method of claim 9, wherein at least one of the time-stamped frame sequences comprises a series of photographs taken by the image capture device or a series of frames from a video recorded by the image capture device.

11. The method of claim 9, wherein the regions of interest comprise a face region, a near-face region, and a background region.

12. The method of claim 9, further comprising estimating a pixel velocity for each pixel within each region of interest, and further wherein the estimated pixel velocities are used to calculate the motion feature for each region of interest.

13. The method of claim 9, wherein the spoofed subject of at least one of the second plurality of time-stamped frame sequences is a printed photo spoof, a shaped board spoof, a printed paper spoof, a displayed static digital image spoof, or a smart phone replay video spoof.

14. The method of claim 9, wherein the spoofed subjects of the second plurality of time-stamped frame sequences comprise different types of spoofs.

15. The method of claim 9, wherein machine learning techniques are used to generate the training rules based on the positive and negative data.

16. A face recognition system comprising:
   an image capture device;
   a processor;
   a face detection unit comprising a memory; and
   a face matching unit;
   wherein the memory stores instructions that, when executed by the processor, cause the processor to:
      receive, from the image capture device, a time-stamped frame sequence;
      identify corresponding pixels for each pair of sequential frames in the time-stamped frame sequence;
      adjust overall intensity of each successive image;
      segment one of each pair of sequential frames in the time-stamped frame sequence into regions of interest;
      calculate a motion feature for each region of interest of each pair of sequential frames in the time-stamped frame sequence, the motion feature at least based on a change in position of a pixel between a pair of sequential frames over a known change in time determined from data within time-stamps of the time-stamped fame sequence;

generate a preliminary face-liveness determination for each pair of sequential frames in the time-stamped frame sequence, based on a comparison of the calculated motion features for the pair of sequential frames; and make a final face-liveness determination based on the generated preliminary face liveness determinations, wherein one or more thresholds for either face-liveness determination are adjusted based on a frame rate at which the time-stamped frame sequence is taken.

17. The system of claim 16, wherein the memory stores additional instructions that, when executed by the processor, further cause the processor to estimate a pixel velocity for each pixel within each region of interest, and further wherein the estimated pixel velocities are used to calculate the motion feature for each region of interest.

18. The system of claim 16, wherein the regions of interest comprise a face region, a near-face region, and a background region.

19. The system of claim 16, wherein the memory stores additional instructions that, when executed by the processor, further cause the processor to provide a face associated with the time-stamped frame sequence to the face matching unit when the final face liveness determination indicates that the face is live.

20. The system of claim 16, wherein the face matching unit comprises a second memory, the second memory storing second instructions that, when executed by the processor, cause the processor to compare a face associated with the time-stamped frame sequence to a plurality of stored faces to identify a matching face.

* * * * *